(12) United States Patent
Strayer et al.

(10) Patent No.: US 11,813,279 B2
(45) Date of Patent: *Nov. 14, 2023

(54) COMPOSITIONS FOR CANCER THERAPY AND METHODS

(71) Applicant: AIM IMMUNOTECH INC., Ocala, FL (US)

(72) Inventors: David R. Strayer, Ocala, FL (US); Thomas K. Equels, Ocala, FL (US)

(73) Assignee: AIM ImmunoTech Inc., Ocala, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/537,442

(22) Filed: Aug. 9, 2019

(65) Prior Publication Data

US 2020/0197433 A1 Jun. 25, 2020

Related U.S. Application Data

(60) Provisional application No. 62/869,909, filed on Jul. 2, 2019, provisional application No. 62/792,796, filed on Jan. 15, 2019, provisional application No. 62/792,786, filed on Jan. 15, 2019, provisional application No. 62/792,783, filed on Jan. 15, 2019, provisional application No. 62/792,778, filed on Jan. 15, 2019, provisional application No. 62/792,765, filed on Jan. 15, 2019, provisional application No. 62/792,812, filed on Jan. 15, 2019, provisional application No. 62/792,788, filed on Jan. 15, 2019, provisional application No. 62/792,770, filed on Jan. 15, 2019, provisional application No. 62/792,791, filed on Jan. 15, 2019, provisional application No. 62/792,760, filed on Jan. 15, 2019, provisional application No. 62/783,834, filed on Dec. 21, 2018.

(51) Int. Cl.
| | |
|---|---|
| *A61K 31/713* | (2006.01) |
| *A61K 38/21* | (2006.01) |
| *A61K 39/395* | (2006.01) |
| *A61P 35/00* | (2006.01) |
| *A61K 9/00* | (2006.01) |
| *A61K 39/00* | (2006.01) |

(52) U.S. Cl.
CPC .......... *A61K 31/713* (2013.01); *A61K 9/0019* (2013.01); *A61K 38/212* (2013.01); *A61K 39/3955* (2013.01); *A61P 35/00* (2018.01); *A61K 2039/505* (2013.01)

(58) Field of Classification Search
CPC ............ A61K 31/713; A61K 2039/505; A61K 39/3955
See application file for complete search history.

(56) References Cited

U.S. PATENT DOCUMENTS 5,595,756 A * 1/1997 Bally ................... A61K 9/1272
264/4.1

FOREIGN PATENT DOCUMENTS

| WO | 2010/047835 A2 | 4/2010 |
|---|---|---|
| WO | 2020132560 A2 | 6/2020 |

OTHER PUBLICATIONS

Desousa et al. Frontiers in Immunology 9:1909 (Year: 2018).*
Rao et al. Sci Transl Med 2017;9:eaah3560 (Year: 2017).*
Jasani et al. Vaccine 27 (2009) 3401-340 (Year: 2009).*
Heppner et al. (Cancer Metastasis Review 2:5-23; 1983 (Year: 1983).*
Jain RK (Scientific American, Jul. 1994, 58-65 (Year: 1994).*
Sporn et al. (Chemoprevention of Cancer, Carcinogenesis, vol. 21 (2000), 525-530 (Year: 2000).*
Auerbach et al. (Cancer and Metastasis Reviews, 2000, 19: 167-172 (Year: 2000).*
Gura T (Science, 1997, 278(5340): 1041-1042, encloses 1-5 (Year: 1997).*
Hait (Nature Reviews/Drug Discovery, 2010, 9, pp. 253-254 (Year: 2010).*
Gravanis et al. (Chin Clin Oncol, 2014, 3, pp. 1-5 (Year: 2014).*
Bean. PNAS 2018; 115(50): 12539-12543 (Year: 2018).*
Oberrnajer et al. (Journal of Immunotherapy of Cancer 2016; 4(Suppl 1):P230 (Year: 2016).*
AIM ImmunoTech Inc. and Merck Sharp & Dohme (Systemic Immune Checkpoint Blockade and Intraperitoneal Chemo-Immunotherapy in Recurrent Ovarian Cancer. Retrieved from https://clinicaltrials.gov/ct2/show/record/NCT03734692. First posted Nov. 8, 2018, ClinicalTrials.gov Identifier: NCT03734692 (Year: 2018).*
Topalian et al. Safety, activity, and immune correlates of anti-PD_1 antibody in cancer. New England Journal of Medicine. 2012; 366(26): 2443-2454 (Year: 2012).*
Fujii et al. Biomarkers of response to immune checkpoint blockade in cancer. Critical Reviews in Oncology/Hematology, 2018; 130: 108-120 (Year: 2018).*
Rao et al. Predictors of response and resitance to checkpoint inhibitors in solid tumors. Ann Transl Med 2017;5(23):468) (Year: 2017).*
Desousa et al. Not All Immune Checkpoints Are Created Equal. Front. Immunol. 9:1909. doi: 10.3389/fimmu.2018.01909 (Year: 2018).*
Heppner et al. Tumor heterogeneity: biological implications and therapeutic consequences. Cancer Metastasis Review 2:5-23; 1983 (Year: 1983).*

(Continued)

*Primary Examiner* — Sandra Dillahunt
(74) *Attorney, Agent, or Firm* — Studebaker & Brackett PC

(57) ABSTRACT

One aspect of this disclosure is directed to a method for treating a cancer in a subject in need thereof by administering to the subject at least a first compound and a second compound together or separately. The first compound is an effective amount of a checkpoint inhibitor optionally with at least one pharmaceutically acceptable carrier. The second compound is an effective amount of an Anti-Tumor Immune Enhancer (ATIE) optionally with at least one pharmaceutically acceptable carrier. The compounds can be administered together or separately.

29 Claims, 9 Drawing Sheets

(56) References Cited

OTHER PUBLICATIONS

Jain RK. Barriers to Drug Delivery in Solid Tumors. Scientific American, Jul. 1994, 58-65 (Year: 1994).*
MacCallum et al. Antibody-antigen interactions: contact analysis and binding topography. Journal of Molecular Biology, 262:732-745, 1996 (Year: 1996).*
Vajdos et al. Comprehensive functional Maps of the antigen-binding site of an anti-ErbB2 antibody obtained with shotgun scanning mutagenesis. Journal of Molecular Biology, Jul. 5, 2002;320(2):415-28 (Year: 2002).*
Ferrara et al. Recombinant renewable polyclonal antibodies. mABs, 2015; 7(1): 32-41 (Year: 2015).*
Jasani et al. Ampligen: A potential toll-like 3 receptor adjuvant for immunotherapy of cancer. Vaccine 27 (2009) 3401-3404 (Year: 2009).*
Topalian et al. New England Journal of Medicine. 2012; 366(26): 2443-2454 (Year: 2012).*
Desousa et al. Front. Immunol. 2018; 9:1909. doi: 10.3389/fimmu.2018.01909 (Year: 2018).*
By Ferrara et al. mABs, 2015; 7(1): 32-41 (Year: 2015).*
Fujii et al. Critical Reviews in Oncology/Hematology, 2018; 130:108-120 (Year: 2018).*
Rao et al. Ann Transl Med 2017;5(23):468 (Year: 2017).*
Desousa et al. Front. Immunol. 2018; 9:1909. doi: 10.3389/fimmu.2018.01909 (Year: 2019).*
Paul. Fundamental Immunology, 3rd Edition, Raven Press, New York, Chapter 8, pp. 292-295, 1993 (Year: 1993).*
MacCallum et al. Journal of Molecular Biology, 262:732-745, 1996 (Year: 1996).*
Vajdos et al. Journal of Molecular Biology, Jul. 5, 2002;320(2):415-28 (Year: 2002).*
Ferrara et al. mABs, 2015; 7(1): 32-41 (Year: 2015).*
Aagaard et al. Advanced Drug Delivery Reviews 59 (2007) 75-86) (Year: 2007).*
Warzocha et al. Leukemia and Lymphoma, 1997; 24(3-4): 267-281 (Year: 1997).*
Guido et al. Curr Med Chem. 2008; 15(1):37-46 (Year: 2008).*
Clark et al. J. Med. Chem., 2014, 57 (12), pp. 5023-5038 (Year: 2014).*
Gayvert KM, Aly O, Platt J, Bosenberg MW, Stern DF, Elemento O (2017) A Computational Approach for Identifying Synergistic Drug Combinations. PLoS Comput Biol 13(1): (Year: 2017).*
Yin Z, Deng Z, Zhao W and Cao Z (2018) Searching Synergistic Dose Combinations for Anticancer Drugs. Front. Pharmacol. 9:535. (Year: 2018).*
Tallarida et al. Pharmacol Ther. Aug. 2010 ; 127(2): 165-174. doi:10.1016/j.pharmthera.2010.04.011 (Year: 2010).*
Oberrnajer et al. Journal of Immunotherapy of Cancer 2016; 4(Suppl 1) (Year: 2016).*
Abdou et al., Chemokine modulation to enhance the effectiveness of pembrolizumab in patients with metastatic triple-negative breast cancer [abstract]. In: Proceedings of the Fourth CRI-CIMT-EATI-AACR International Cancer Immunotherapy Conference: Translating Science into Survival; Sep. 30-Oct 3, 2018; New York, NY, Philadelphia, PA: AACR; Cancer Immunol Res 2019.
Casey Ager, et al., Journal For Immunotherapy Of Cancer (2016), vol. 4, pp. 107-221.
Press Release: Hemispherx Announces New Data Showing Ampligen's Positive Role in Reprograming Tumor Microenvironment—Study Results Suggests Ampligen Could Materially Enhance the Effectiveness of Checkpoint Blockade Technology (Jun. 5, 2018), pp. 1-3, Retrieved from the Internet: URL:https://www.globenewswire.com/news-release/2018/06/05/1517183/0/en/Hemispherx-Announces-New-Data-Showing-Ampligen-s-Positive-Role-in-Reprograming-Tumor-Microenvironment.html [retrieved on Mar. 10, 2020].
Marie-Nicole Theodoraki, et al., Helicase-Driven Activation of NF kappa B-COX2 Pathway Mediates the Immunosuppressive Component of dsRNA-Driven Inflammation in the Human Tumor Microenvironment, Cancer Research, (2018) vol. 78, No. 15, pp. 4292-4302.
Abdou Y, et al., Chemokine modulation to enhance the effectiveness of pembrolizumab in patients with metastatic triple-negative breast cancer. Cancer Research 79 (2019) (4 Supplement) pp. Abstract OT2-06-02.
Anonymous: Table of Contents : Cancer Immunology Research 11 (2019) pp. 1-5. Retrieved from the Internet: <URL:https://cancerimmunolres.aacrjournals>.org/content/7/2 Supplement [retrieved on Mar. 10, 2020].
Anonymous: Table of Contents—Trials in Progress : Cancer Immunology Research 11 (2019) pp. 1-4, Retrieved from the Internet: < URL:https://cancerimmunolres.aacrjournals>.org/search/volume7%20issue:2+Supplement%2Ojcode:canimm?facet toe-section-id! O !=Trials%20in%20Progress:%20Poster%20Pres entations%20-%20Proffered%20Abstracts [retrieved on Mar. 10, 2020].
Anonymous: Systemic Immune Checkpoint Blockade and Intraperitoneal Chemo-Immunotherapy in Recurrent Ovarian Cancer (2018) pp. 1-8. Retrieved from the Internet: < URL:https://clinicaltrials.gov/ct2/history>/NCT03734692?V2=View#StudyPageTop [retrieved on Mar. 10, 2020].
Anonymous: Immuno-Oncology Summit (2016), pp. 1-27. Retrieved from the Internet: < URL:https://www.immuno-oncologysummit.com/> uploadedFiles/Immuno Oncology Summit/Agenda/16/2016-The-Immuno~Oncology~Summit-Brochure.pdf [retrieved on Mar. 11, 2020].
Christopher F. Nicodemus et al., Toll-like receptor-3 as a target to enhance bioactivity of cancer immunotherapy; American Journal of Obstetrics & Gynecology (2010) vol. 202, No. 6, pp. 608.e1-608.e8.
Annika De Sousa Linhares et al., Not All Immune Checkpoints Are Created Equal; Frontiers In Immunology (2018) vol. 9, pp. 1-15.
Aura Agresta et al., The Emerging Role of CD244 Signaling in Immune Cells of theTumor Microenvironment; Frontiers In Immunology (2018), vol. 9, pp. 1-9.
International Search Report issued in PCT/US2019/068044; dated Jun. 23, 2020.
Written Opinion issued in PCT/US2019/068044; dated Jun. 23, 2020.
Anonymous, "Systemic Immune Checkpoint Blockade and Intraperitoneal Chemo-Immunotherapy in Recurrent Ovarian Cancer," Study NCT03734692 (v2), Dec. 6, 2018, pp. 1-8.

* cited by examiner

As well as time to tumor progression:

COMPOSITIONS FOR CANCER THERAPY AND METHODS

CROSS-REFERENCE TO RELATED APPLICATIONS

This Application claims the benefit of priority to the following applications: U.S. Provisional Application Ser. No. 62/869,909, filed Jul. 2, 2019, entitled "Synergistic Cancer Compositions and Methods Involving Same"; U.S. Provisional Application Ser. No. 62/792,770, filed 15 Jan. 2019, entitled "Pancreatic Cancer Treatment"; U.S. Provisional Application Ser. No. 62/792,788, filed 15 Jan. 2019, entitled "Melanoma Treatment"; U.S. Provisional Application Ser. No. 62/792,796, filed 15 Jan. 2019, entitled "Colorectal Cancer Treatment"; U.S. Provisional Application Ser. No. 62/792,783, filed 15 Jan. 2019, entitled "Ovarian Cancer Treatment"; U.S. Provisional Application Ser. No. 62/792,812, filed 15 Jan. 2019, entitled "Triple Negative Breast Cancer Treatment"; U.S. Provisional Application Ser. No. 62/792,786, filed 15 Jan. 2019, entitled "Bladder Cancer Treatment"; U.S. Provisional Application Ser. No. 62/792,791, filed 15 Jan. 2019, entitled "Kidney Cancer Treatment"; U.S. Provisional Application Ser. No. 62/792,778, filed 15 Jan. 2019, entitled "Lung Cancer Treatment"; U.S. Provisional Application Ser. No. 62/792,765, filed 15 Jan. 2019, entitled "Cancer Treatment Compositions and Methods"; U.S. Provisional Application Ser. No. 62/792,760, filed 15 Jan. 2019, entitled "Cancer Treatment Compositions and Methods"; U.S. Provisional Application Ser. No. 62/783,834, filed 21 Dec. 2018, entitled "Cancer Treatment".

All publications, patent applications, and patents mentioned herein are hereby incorporated by reference in their entirety as if each individual publication or patent was specifically and individually indicated to be incorporated by reference. In case of conflict, the present application, including any definitions herein, will control.

BACKGROUND

Immunotherapy is a rapidly growing field for the treatment of cancers, which, unfortunately, has experienced limited success. A growing arsenal of new drugs that unleash the body's immune system against tumors has captured the cancer treatment spotlight. Immunotherapy has had success in survival or symptom-free windows of time in a minority of patients. Unfortunately, immunotherapies help only a minority of patients with a given cancer type, and, in some types of cancer's, they have had little or no success.

There is a need to develop methods and combination therapies to initiate or enhance the effectiveness of the checkpoint inhibitors in both the nonresponding subject population and the responding subject population. There is a long-felt need to discover why immunotherapies fail for some types of cancer and how they can be improved to work on more types of cancers.

BRIEF SUMMARY

One aspect is directed to a method for treating cancer in a subject in need thereof. The method comprises administering to the subject at least a first compound and a second compound together or separately. The first compound is an effective amount of a checkpoint inhibitor optionally with at least one pharmaceutically acceptable carrier. The second compound is an effective amount of an Anti-Tumor Immune Enhancer (ATIE) optionally with at least one pharmaceutically acceptable carrier.

Another aspect is directed to a method for inhibiting the proliferation of a tumor in a subject in need thereof. The method comprises administering to the subject at least a first compound and a second compound together or separately. The first compound is an effective amount of a checkpoint inhibitor optionally with at least one pharmaceutically acceptable carrier. The second compound is an effective amount of an Anti-Tumor Immune Enhancer (ATIE) optionally with at least one pharmaceutically acceptable carrier.

Another aspect is directed to a method for enhancing or prolonging the effects of a checkpoint inhibitor in a subject in need thereof. The method comprises administering to the subject at least a first compound and a second compound together or separately. The first compound is an effective amount of a checkpoint inhibitor optionally with at least one pharmaceutically acceptable carrier. The second compound is an effective amount of an Anti-Tumor Immune Enhancer (ATIE) optionally with at least one pharmaceutically acceptable carrier.

Another aspect is directed to a method for activating a response to a checkpoint inhibitor in a subject in need thereof. The method comprises administering to the subject at least a first compound and a second compound together or separately. The first compound is an effective amount of a checkpoint inhibitor optionally with at least one pharmaceutically acceptable carrier. The second compound is an effective amount of an Anti-Tumor Immune Enhancer (ATIE) optionally with at least one pharmaceutically acceptable carrier.

In this disclosure, the term "in any aspect of the disclosure" is understood to comprise at least the meaning of "in any of the methods and compositions of this disclosure." In any aspect of this disclosure, the cancer may be selected from the group consisting of: pancreatic cancer, skin cancer, colorectal cancer, ovarian cancer, breast cancer, triple negative breast cancer, bladder cancer, renal cell carcinoma, and lung cancer. In any of aspect of this disclosure, the tumor may be selected from the group consisting of: pancreatic tumor, melanoma, colorectal tumor, ovarian tumor, breast tumor, triple negative breast tumor, bladder tumor, renal tumor, and lung tumor. The cancer may be malignant or nonmalignant or the cancer may be metastatic, or nonmetastatic. Further, the cancer may be within an organ, part of an organ, or outside an organ. For example, the cancer may be within the pancreas, part of the pancreas, outside the pancreas; within the skin, part of the skin, outside the skin; within the colorectal area (colon or rectum), part of the colorectal area, outside the colorectal area; within the bladder, part of the bladder, outside the bladder; within the ovary, part of the ovary, outside the ovary; within the breast, part of the breast, outside the breast; within the kidney, part of the kidney, outside the kidney; within the lung, part of the lung, outside the lung.

In any part of this disclosure, including the methods and compositions, the ATIE may be AMPLIGEN. The effective amount of ATIE is a synergistic, therapeutically effective amount that is synergistic with a blockade inhibitor (also referred to in this disclosure as an immune checkpoint inhibitor). In a non-limiting example, the ATIE may be a dsRNA (e.g., AMPLIGEN). The dsRNA may be at least one selected from the group consisting of: $rI_n \cdot ribo(C_4U)_n$; $rI_n \cdot ribo(C_5U)_n$; $rI_n \cdot ribo(C_6U)_n$; $rI_n \cdot ribo(C_7U)_n$; $rI_n \cdot ribo(C_8U)_n$; $rI_n \cdot ribo(C_9U)_n$; $rI_n \cdot ribo(C_{10}U)_n$; $rI_n \cdot ribo(C_{11}U)_n$; $rI_n \cdot ribo(C_{12}U)_n$; $rI_n \cdot ribo(C_{13}U)_n$; $rI_n \cdot ribo(C_{14}U)_n$; $rI_n \cdot ribo$ $(C_{15}U)_n$; $rI_n \cdot ribo(C_{16}U)_n$; $rI_n \cdot ribo(C_{17}U)_n$; $rI_n \cdot ribo(C_{18}U)_n$; $rI_n \cdot ribo(C_{19}U)_n$; $rI_n \cdot ribo(C_{20}U)_n$; $rI_n \cdot ribo(C_{21}U)_n$; $rI_n \cdot ribo(C_{22}U)_n$; $rI_n \cdot ribo(C_{23}U)_n$; $rI_n \cdot ribo(C_{24}U)_n$; $rI_n \cdot ribo(C_{25}U)_n$; $rI_n \cdot ribo(C_{26}U)_n$; $rI_n \cdot ribo(C_{27}U)_n$; $rI_n \cdot ribo(C_{28}U)_n$; $rI_n \cdot ribo(C_{29}U)_n$; $rI_n \cdot ribo(C_{30}U)_n$; $rI_n \cdot ribo(C_{31}U)_n$; $rI_n \cdot ribo(C_{32}U)_n$; $rI_n \cdot ribo(C_{33}U)_n$; $rI_n \cdot ribo(C_{34}U)_n$; $rI_n \cdot ribo(C_{35}U)_n$; $rI_n \cdot r(C_{p-23}, G_{>p})_n$; $rI_n \cdot ribo(C_{4-29}U)_n$; $rI_n \cdot r(C_{11-14}U)_n$; $rI_n \cdot ribo(C_{30-35}U)_n$; rugged dsRNA; and $r(Poly\,A \cdot Poly\,U)_n$.

In any of the methods and compositions of this application, the ATIE and the checkpoint inhibitor administered may provide a synergistic effect in the treatment of cancer or the inhibition of the proliferation of tumor cells. Synergism refers to, for example, when compound "a" provides an effect of 1 and compound "b" provides an effect of 0.1 but together compounds "a" and "b" provides an effect that is greater than 1.1 (i.e., a+b) such as 1.2, 1.3, 1.5, 1.7, or 2 or more than any of the listed numbers. As another example, synergism refers to, for example, when compound "c" provides an effect of 1 and compound "d" provides an effect of 1 but together compounds "c" and "d" provides an effect that is greater than 2 (i.e., c+d) such as 2.2, 2.3, 2.5, 2.7, 3, 4, 5, 8 or more than any of the listed numbers. As another example of synergism, the synergism may refer to an amount of a compound a that is ineffective by itself, an amount of compound b that is ineffective by itself, but when the same amounts of a and b are combined, the combination is effective for treating a cancer or a tumor.

The synergistic effect, as disclosed anywhere in this specification, may be selected from the group consisting of inhibiting tumor growth; inducing tumor cell death; increasing tumor regression; preventing or delaying tumor recurrence; preventing or delaying tumor growth; preventing or delaying tumor spread, and promoting tumor elimination.

In any part of this disclosure, the effective amount of checkpoint inhibitor may be a synergistic, therapeutically effective amount. In any part of this disclosure, the checkpoint inhibitor administered provides an additive or synergistic effect in the treatment of cancer or inhibition of the proliferation of a tumor.

In any part of this disclosure, the ATIE and the checkpoint inhibitor may be administered together at the same time or administered separately (e.g., within two hours but also within a range of periods are also envisioned).

In any of the methods, an optional third compound or compounds may be administered. In any of the compositions of the disclosure, an optional third compound may be added. Therefore, in any of the methods, the method may further comprise administering to the subject a optional third compound wherein the optional third compound is one or more selected from the group consisting of: a chemotherapeutic drug, a targeted drug anti-cancer drug, and a targeted anti-cancer drug comprising an antibody. The effective amount of optional third compound is a synergistic, therapeutically effective amount. That is, the optional third compound may act synergistically with the ATIE, with the checkpoint inhibitor, or with both.

For example, in one aspect, the method comprises the steps of administering to the subject one or more selected from the group consisting of: an interferon, interferon mixture, Alferon, and alpha-interferon species. The method of claim 15 wherein the alpha-interferon species were purified as a mixture of at least seven species of α-interferon produced by human white blood cells. The seven species may be α2, α4, α7, α8, α10, α16 and α17.

Administrating and/or administration may be performed intravenously or by any administration methods.

In one aspect of the methods of this disclosure, the ATIE and the checkpoint inhibitor, and the optional third compound if an optional third compound is used, are administered together. In another aspect of the methods of this disclosure, the ATIE and the checkpoint inhibitor, and the optional third compound if an optional third compound is used, are administered separately. In another aspect of the methods of this disclosure, the ATIE and the checkpoint inhibitor, and the optional third compound if an optional third compound is used, are administered separately but within a time period selected from the group consisting of: 1 month, 1 week, 3 days, 1 day, 12 hours, 6 hours, 3 hours, 2 hours, 1 hour, 30 minutes, 15 minutes, or 5 minutes.

In any aspect of this disclosure, at least two of the compounds such as the ATIE and the checkpoint inhibitor, and the optional third compound if an optional third compound is used, can be mixed into the same compound. An as a further nonbinding example, a compounds (e.g., comprising the ATIE and the checkpoint inhibitor) can be administered to a subject and thereby both the ATIE and the checkpoint inhibitor in this example are administered together. In any aspects of this disclosure, where an optional third compound is used, the composition may be, for example, ATIE+checkpoint inhibitor; ATIE+optional third compound; checkpoint inhibitor+optional third compound; or ATIE+checkpoint inhibitor+optional third compound.

As discussed above, in any aspect of this disclosure, the ATIE and the checkpoint inhibitor together provides a synergistic effect in the treatment of pancreatic cancer or in an inhibition of the proliferation of tumor cells over the use of ATIE alone; checkpoint inhibitor alone; or sum of ATIE alone and checkpoint inhibitor alone.

Also, in any aspect of this disclosure, the ATIE, the checkpoint inhibitor, and the optional third compound together provides a synergistic effect in the treatment of cancer or in an inhibition of the proliferation of tumor cells over the use of (1) ATIE alone; (2) checkpoint inhibitor alone; (3) the optional third compound alone; or (4) the sum of (ATIE+checkpoint inhibitor+optional third compound).

In any aspect of this disclosure, the checkpoint inhibitor may have has at least one characteristic selected from the group consisting of: an antibody, a monoclonal antibody, a humanized antibody, a fully human antibody, a fusion protein, a PEGylated antibody, a multimeric antibody, and a combination thereof.

In any aspect of this disclosure, the checkpoint inhibitor may inhibit or interact with a ligand of a checkpoint protein selected from the group consisting of: 2B4; A2aR; B-7 family ligand; B7-H3; B7-H4; Band T lymphocyte attenuator (BTLA); BMA; CD112; CD137; CD160; CD2; CD20; CD226; CD27; CD276; CD28; CD30; CD33; CD40; CD47; CD52; CD70; CD80; CD86; CGEN-15049; CHK 1; CHK2; cytotoxic T-lymphocyte antigen-4 (CTLA-4); DR3; galectin 9 (GALS); GITR; herpesvirus entry mediator (HVEM); HVEM; ICOS; IDO1; IDO2; Killer-Cell Immunoglobulin-Like Receptor (KIR); LAG3; LAIR; LAIR1; LAIR2; LIGHT; lymphocyte activation gene 3 (LAG-3); MARCO; OX-40; PD-1; PD-L1; PD-L2; PS; SIRP alpha; SLAM; T cell immunoreceptor with Ig and ITIM domains (TIGIT); T cell membrane protein 3 (TIM3); V-domain immunoglobulin (Ig)-containing suppressor of T-cell activation (VISTA); VTCN1; and a combination thereof.

In any aspect of this disclosure, the checkpoint inhibitor may be selected from the group consisting of: alemtuzumab (CAMPATH-1H®); AMP-224 (GlaxoSmithKline/Amplimmune); AMP-514 (Amplimmune/AZ); arelumab (Merck Serono); atezolizumab (TECENTRIQ®); AUNP 12 (Aurigene and Pierre Fabre); avelumabBMS-936559 BMS-986016 (Bristol-Meyers Squibb); cemiplimab) (LIBTAYO®) ; CP-870;893 (Genentech); CT-011, durvalumab (IMFINIZI®); Galiximab (Biogen Idec); IMP321 (Immutep S.A.); INCB024360 (Incyte)Indoximod (NewLink Genetics); IPH2101 (Innate Pharma/Bristol-Myers Squibb); ipilimumab (YERVOY®); lambrolizumab, lirilumab (Bristol-Myers Squibb); MDX-1105 (Medarex; Inc;/Bristol Myer Squibb); MEDI-4736 (Medimmune/AstraZeneca); MEDI-6469 (MedImmune/AZ); MGA271 (Macrogenics); MIHI; Mogamulizumab (Kyowa Hakko Kirin); MPDL3280A (Roche); nivolumab (Bristol-Myers Squibb); NLG-919 (NewLink Genetics); ofatumumab (ARZERRA®); pembrolizumab (KEYTRUDA®); PF-05082566 (Pfizer); pidilizumab (Curetech); rituximab (RITUXAN®); tremelimumab (formerly ticilimumab; CP-675;206); urelumab (Bristol-Meyers Squibb); Varlilumab (CellDex Therapeutics); and a combination thereof.

In any aspect of this disclosure, the compound or composition may be a solid or a liquid compound or composition.

In any aspect of this disclosure, the subject may be a human, a mammal, an animal, or a combination thereof including any animals, mammals or humans disclosed in this disclosure.

Another aspect of this disclosure relates to a composition for treating pancreatic cancer comprising: a checkpoint inhibitor, an ATIE, and optionally at least one pharmaceutically acceptable carrier. In any aspect of this disclosure, the composition may improve progression free survival or life expectancy of a patient administered the composition. In any aspect of this disclosure, the checkpoint inhibitor may be one or more selected from the group consisting of: a monoclonal antibody, a humanized antibody, a fully human antibody, a fusion protein, and any combination thereof. In any aspect of this disclosure, the checkpoint inhibitor inhibits or interacts with a ligand of a checkpoint protein selected from the group consisting of: 2B4; A2aR; B-7 family ligand; B7-H3; B7-H4; B and T lymphocyte attenuator (BTLA); BMA; CD112; CD137; CD160; CD2; CD20; CD226; CD27; CD276; CD28; CD30; CD33; CD40; CD47; CD52; CD70; CD80; CD86; CGEN-15049; CHK 1; CHK2; cytotoxic T-lymphocyte antigen-4 (CTLA-4); DR3; galectin 9 (GALS); GITR; herpesvirus entry mediator (HVEM); HVEM; ICOS; IDO1; IDO2; Killer-Cell Immunoglobulin-Like Receptor (KIR); LAG3; LAIR; LAIR1; LAIR2; LIGHT; lymphocyte activation gene 3 (LAG-3); MARCO; OX-40; PD-1; PD-L1; PD-L2; PS; SIRP alpha; SLAM; T cell immunoreceptor with Ig and ITIM domains (TIGIT); T cell membrane protein 3 (TIM3); V-domain immunoglobulin (Ig)-containing suppressor of T-cell activation (VISTA); VTCN1; and a combination thereof.

In any aspect of this disclosure, when a reference to a checkpoint inhibitor (also called an immune checkpoint inhibitor) is made and including reference to drugs/antibodies/agonist/antagonist or anything that interacts with a checkpoint inhibitor, the checkpoint inhibitor may be selected from any checkpoint inhibitor in any part of this disclosure including the group consisting of: alemtuzumab (CAMPATH-1H®); AMP-224 (GlaxoSmithKline/Amplimmune); AMP-514 (Amplimmune/AZ); arelumab (Merck Serono); atezolizumab (TECENTRIQ®); AUNP 12 (Aurigene and Pierre Fabre); avelumabBMS-936559 BMS-986016 (Bristol-Meyers Squibb); cemiplimab) (LIBTAYO®) ; CP-870;893 (Genentech); CT-011, durvalumab (IMFINIZI®); Galiximab (Biogen Idec); IMP321 (Immutep S.A.); INCB024360 (Incyte)Indoximod (NewLink Genetics); IPH2101 (Innate Pharma/Bristol-Myers Squibb); ipilimumab (YERVOY®); lambrolizumab, lirilumab (Bristol-Myers Squibb); MDX-1105 (Medarex; Inc;/Bristol Myer Squibb); MEDI-4736 (Medimmune/AstraZeneca); MEDI-6469 (MedImmune/AZ); MGA271 (Macrogenics); MIHI; Mogamulizumab (Kyowa Hakko Kirin); MPDL3280A (Roche); nivolumab (Bristol-Myers Squibb); NLG-919 (NewLink Genetics); ofatumumab (ARZERRA®); pembrolizumab (KEYTRUDA®); PF-05082566 (Pfizer); pidilizumab (Curetech); rituximab (RITUXAN®); tremelimumab (formerly ticilimumab; CP-675;206); urelumab (Bristol-Meyers Squibb); Varlilumab (CellDex Therapeutics); and a combination thereof.

In any aspect of this disclosure, the chemotherapeutic drug may be at least one selected from the group consisting of ABVD; AC; ACE; Abiraterone (Zytiga); Abraxane; Abstral; Actinomycin D; Actiq; Adriamycin; Afatinib (Giotrif); Afinitor; Aflibercept (Zaltrap); Aldara; Aldesleukin (IL-2, Proleukin or interleukin 2); Alemtuzumab (MabCampath); Alkeran; Amsacrine (Amsidine, m-AMSA); Amsidine; Anastrozole (Arimidex); Ara C; Aredia; Arimidex; Aromasin; Arsenic trioxide (Trisenox, ATO); Asparaginase (Crisantaspase, Erwinase); Axitinib (Inlyta); Azacitidine (Vidaza); BEACOPP; BEAM; Bendamustine (Levact); Bevacizumab (Avastin); Bexarotene (Targretin); Bicalutamide (Casodex); Bleomycin; Bleomycin, etoposide and platinum (BEP); Bortezomib (Velcade); Bosulif; Bosutinib (Bosulif); Brentuximab (Adcetris); Brufen; Buserelin (Suprefact); Busilvex; Busulfan (Myleran, Busilvex); CAPE-OX; CAPDX; CAV; CAVE; CCNU; CHOP; CMF; CMV; CVP; Cabazitaxel (Jevtana); Cabozantinib (Cometriq); Caelyx; Calpol; Campto; Capecitabine (Xeloda); Caprelsa; Carbo MV; CarboTaxol; Carboplatin; Carboplatin and etoposide; Carboplatin and paclitaxel; Carmustine (BCNU, Gliadel); Casodex; Ceritinib (Zykadia); Cerubidin; Cetuximab (Erbitux); ChIVPP; Chlorambucil (Leukeran); Cisplatin; Cisplatin and Teysuno; Cisplatin and capecitabine (CX); Cisplatin, etoposide and ifosfamide (PEI); Cisplatin, fluorouracil (5-FU) and trastuzumab; Cladribine (Leustat, LITAK); Clasteon; Clofarabine (Evoltra); Co-codamol (Kapake, Solpadol, Tylex); Cometriq; Cosmegen; Crisantaspase; Crizotinib (Xalkori); Cyclophosphamide; Cyclophosphamide, thalidomide and dexamethasone (CTD); Cyprostat; Cyproterone acetate (Cyprostat); Cytarabine (Ara C, cytosine arabinoside); Cytarabine into spinal fluid; Cytosine arabinoside; DHAP; DTIC; Dabrafenib (Tafinlar); Dacarbazine (DTIC); Dacogen; Dactinomycin (actinomycin D, Cosmegen); Dasatinib (Sprycel); Daunorubicin; De Gramont; Decapepty SR; Decitabine (Dacogen); Degarelix (Firmagon); Denosumab (Prolia, Xgeva); Depocyte; Dexamethasone; Diamorphine; Disodium pamidronate; Disprol; Docetaxel (Taxotere); Docetaxel, cisplatin and fluorouracil (TPF); Doxifos; Doxil; Doxorubicin (Adriamycin); Doxorubicin and ifosfamide (Doxifos); Drogenil; Durogesic; EC; ECF; EOF; EOX; EP (Etoposide and cisplatin); ESHAP; Effentora; Efudix; Eldisine; Eloxatin; Enzalutamide; Epirubicin (Pharmorubicin); Epirubicin cisplatin and capecitabine (ECX); Epirubicin, carboplatin and capecitabine (ECarboX); Eposin; Erbitux; Eribulin (Halaven); Erlotinib (Tarceva); Erwinase; Estracyt; Etopophos; Etoposide (Eposin, Etopophos, Vepesid); Everolimus (Afinitor); Evoltra; Exemestane (Aromasin); FAD; FEC; FEC-T chemotherapy; FMD; FOLFIRINOX; FOLFOX; Faslodex; Femara; Fentanyl; Firmagon; Fludara; Fludarabine (Fludara); Fludarabine, cyclophosphamide and rituximab (FCR); Fluorouracil (5FU); Flutamide; Folinic acid, fluorouracil and irinotecan (FOLFIRI); Fulvestrant (faslodex); G-CSF; Gefitinib (Iressa); GemCarbo (gemcitabine and carboplatin); GemTaxol; Gemcitabine (Gemzar); Gemcitabine and capecitabine (GemCap); Gemcitabine and cisplatin (GC); Gemcitabine and paclitaxel (GemTaxol); Gemzar; Giotrif; Gliadel; Glivec; Gonapeptyl Depot; Goserelin (Zoladex); Goserelin (Zoladex, Novgos); Granulocyte colony stimulating factor (G-CSF); Halaven; Herceptin; Hycamtin; Hydrea; Hydroxycarbamide (Hydrea); Hydroxyurea; I-DEX; ICE; IL-2; IPE; Ibandronic acid; Ibritumomab (Zevalin); Ibrutinib (Imbruvica); Ibuprofen (Brufen, Nurofen); Iclusig; Idarubicin (Zavedos); Idarubicin and dexamethasone; Idelalisib (Zydelig); Ifosfamide (Mitoxana); Imatinib (Glivec); Imiquimod cream (Aldara); Imnovid; Instanyl; Interferon (Intron A); Interleukin; Intron A; Ipilimumab (Yervoy); Iressa; Irinotecan (Campto); Irinotecan and capecitabine (Xeliri); Irinotecan de Gramont; Irinotecan modified de Gramont; Javlor; Jevtana; Kadcyla; Kapake; Keytruda; Lanreotide (Somatuline); Lanvis; Lapatinib (Tyverb); Lenalidomide (Revlimid); Letrozole (Femara); Leukeran; Leuprorelin (Prostap, Lutrate); Leustat; Levact; Liposomal doxorubicin; Litak; Lomustine (CCNU); Lynparza; Lysodren; MIC; MMM; MPT; MST Continus; MVAC; MVP; MabCampath; Mabthera; Maxtrex; Medroxyprogesterone acetate (Provera); Megace; Megestrol acetate (Megace); Melphalan (Alkeran); Mepact; Mercaptopurine (Xaluprine); Methotrexate; Methyl prednisolone; Mifamurtide (Mepact); Mitomycin C; Mitotane; Mitoxana; Mitoxantrone (Mitozantrone); Morphgesic SR; Morphine; Myleran; Myocet; Nabpaclitaxel; Nab-paclitaxel (Abraxane); Navelbine; Nelarabine (Atriance); Nexavar; Nilotinib (Tasigna); Nintedanib (Vargatef); Nipent; Nivolumab (Opdivo); Novgos; Nurofen; Obinutuzumab (Gazyvaro); Octreotide; Ofatumumab (Arzerra); Olaparib (Lynparza); Oncovin; Onkotrone; Opdivo; Oramorph; Oxaliplatin (Eloxatin); Oxaliplatin and capecitabine (Xelox); PAD; PC (paclitaxel and carboplatin, CarboTaxol); PE; PMitCEBO; POMB/ACE; Paclitaxel (Taxol); Paclitaxel and carboplatin; Pamidronate; Panadol; Panitumumab (Vectibix); Paracetamol; Pazopanib (Votrient); Pembrolizumab (Keytruda); Pemetrexed (Alimta); Pemetrexed and carboplatin; Pemetrexed and cisplatin; Pentostatin (Nipent); Perjeta; Pertuzumab (Perjeta); Pixantrone (Pixuvri); Pixuvri; Pomalidomide (Imnovid); Ponatinib; Potactasol; Prednisolone; Procarbazine; Procarbazine, lomustine and vincristine (PCV); Proleukin; Prolia; Prostap; Provera; Purinethol; R-CHOP; R-CVP; R-DHAP; R-ESHAP; R-GCVP; RICE; Raloxifene; Raltitrexed (Tomudex); Regorafenib (Stivarga); Revlimid; Rituximab (Mabthera); Sevredol; Sodium clodronate (Bonefos, Clasteon, Loron); Solpadol; Sorafenib (Nexavar); Steroids (dexamethasone, prednisolone, methylprednisolone); Streptozocin (Zanosar); Sunitinib (Sutent); Sutent; TAC; TIP; Tafinlar; Tamoxifen; Tarceva; Targretin; Tasigna; Taxol; Taxotere; Taxotere and cyclophosphamide (TC); Temodal; Temozolomide (Temodal); Temsirolimus; Tepadina; Teysuno; Thalidomide; Thiotepa (Tepadina); Tioguanine (thioguanine, 6-TG, 6-tioguanine); Tomudex; Topotecan (Hycamtin, Potactasol); Torisel; Trabectedin (Yondelis); Trastuzumab (Herceptin); Trastuzumab emtansine (Kadcyla); Treosulfan; Tretinoin (Vesanoid, ATRA); Triptorelin; Trisenox; Tylex; Tyverb; VIDE; Vandetanib (Caprelsa); Vargatef; VeIP; Vectibix; Velbe; Velcade; Vemurafenib (Zelboraf); Vepesid; Vesanoid; Vidaza; Vinblastine (Velbe); Vincristine; Vincristine, actinomycin D (dactinomycin) and cyclophosphamide (VAC); Vincristine, actinomycin and ifosfamide (VAI); Vincristine, doxorubicin and dexamethasone (VAD); Vindesine (Eldisine); Vinflunine (Javlor); Vinorelbine (Navelbine); Vismodegib (Erivedge); Votrient; XELOX; Xalkori; Xeloda; Xgeva; Xtandi; Yervoy; Yondelis; Z-DEX; Zaltrap; Zanosar; Zavedos; Zelboraf; Zevalin; Zoladex (breast cancer); Zoladex (prostate cancer); Zoledronic acid (Zometa); Zometa; Zomorph; Zydelig; and Zytiga.

In one aspect of the disclosure, the chemotherapeutic drug is not an immune checkpoint inhibitor. In another aspect of the disclosure, the chemotherapeutic drug is an immune checkpoint inhibitor. In another aspect of the disclosure, the chemotherapeutic drug is a second immune checkpoint inhibitor which targets the same or a different immune checkpoint molecule from the first immune checkpoint inhibitor.

DETAILED DESCRIPTION

Figure 1:
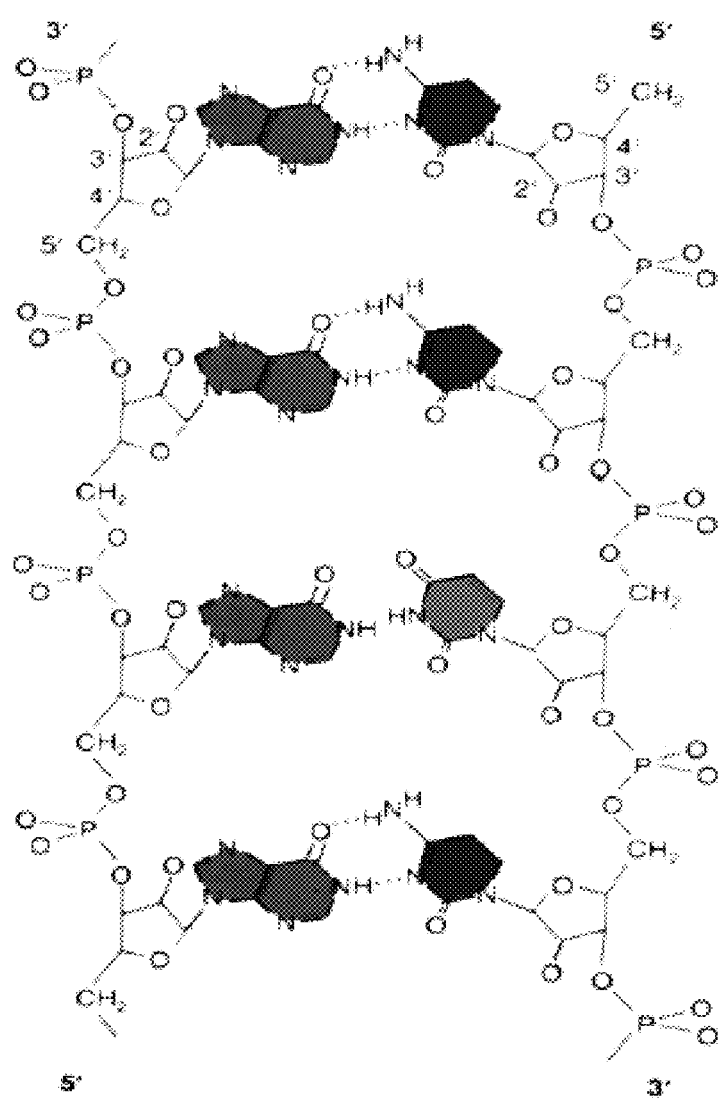
FIG. 1 depicts a part of one embodiment of AMPLIGEN.

Immunotherapy comprising a variety of specific indications are being rapidly approved currently by the FDA for checkpoint inhibitors (monoclonal antibodies which block either T-cell or tumor cell inhibitors of immune elimination). The table lists current FDA approvals for checkpoint inhibitors and are not included in the nonlimiting examples below.

Nonlimiting examples of specific cancer types in need of improved immunotherapy include:

Pancreatic Cancer

Pancreatic cancer is the fourth most common cause of cancer-related deaths in the United States and the eighth most common worldwide. It has one of the highest fatality rates of all cancers and is the fourth highest cancer killer among men and women. For all stages combined, the 1- and 5-year relative survival rates are shockingly low: 25% and 6%, respectively. For local disease, the 5-year survival rate is approximately 20%. The median survival rates for locally advanced and metastatic diseases, which collectively represent over 80% of individuals, are about 10 and 6 months, respectively.

Treatment of pancreatic cancer depends on the stage of the cancer. Although only localized cancer is considered suitable for surgery with curative intent at present, only about 0.20% of cases present with localized disease at diagnosis. Surgery can also be performed for palliation if the malignancy is invading or compressing the duodenum or colon. In such cases, bypass surgery might overcome the obstruction and improve quality of life but is not intended as a cure. For a disease that is deemed not suitable for resection, palliative chemotherapy may be used to improve the quality of life and gain a modest survival benefit for the patient.

There is a need for improved methods for treating pancreatic cancer, in particular, locally advanced and metastatic pancreatic cancer. Metastasis is the leading cause of mortality in cancer patients. However, there are no effective therapies to target the development and progression of metastases in pancreatic cancer.

Melanoma

Globally, melanoma is diagnosed with an incidence rate of 3.0 in 100,000, representing 1.7% of all cancer cases. In 2012, 232,000 women were diagnosed with melanoma. The mortality rate of 0.7 in 100,000 women is substantially lower than the incidence rate (Ferlay et al., 2013). The lifetime risk of getting melanoma is about 2.4% (1 in 40) for Caucasians, 0.1% (1 in 1,000) for African-Americans, and 0.5% (1 in 200) for Hispanics. Although the average age at melanoma diagnosis is 62, it is one of the most common cancers in young adults (especially young women) (American Cancer Society, 2015).

For patients with localized melanoma, the prognosis is good with adequate surgical excision, which is reflected in a relatively low mortality rate (World Cancer Report, 2014). The 5-year survival rate is more than 90% and 80% for stage I and II lesions, respectively (Kaufman et al., 2013).

Metastatic melanoma is, however, largely resistant to current therapies (World Cancer Report, 2014). The 5-year survival rate is 78-40% for stage IIIA-C and 15-20% for stage IV (American Cancer Society, 2015).

Besides sun-exposure, the risk to develop melanoma is influenced by other environmental factors such as age and sex as well as anatomical location and individual susceptibility. Ultraviolet-emitting tanning devices also increase the risk of malignant melanoma. In 20-40% of people with melanoma in their family history, CDKN2A mutations have been found (World Cancer Report, 2014).

Melanomas occur primarily in the skin—more than 95% of cases—but are also found in the mucous membranes of the mouth, nose, anus, and vagina and, to a lesser extent, the intestine. Furthermore, melanocytes are present in the conjunctiva, the retina, and the meninges. Melanoma can be subtyped histologically into superficial spreading melanoma, nodular melanoma, acral lentiginous melanoma, and lentigo maligna melanoma. Melanomas are classified according to the TNM classification. As recommended in the American Joint Committee on Cancer staging manual, melanoma patients are categorized into three groups: localized disease with no evidence of metastases (stage I-II), regional disease (stage III), and distant metastatic disease (stage IV) (World Cancer Report, 2014).

The standard therapy in melanoma is complete surgical resection with surrounding healthy tissue. If resection is not complete or not possible at all, patients receive primary radiation therapy, which can be combined with interferon-alpha administration in advanced stages (stages IIB/C and IIIA-C). Therapeutic options include mono-chemotherapy, poly-chemotherapy. and targeted therapies with specific inhibitors. Dacarbazine, temozolamide. and fotemustin are currently used in mono-chemotherapy trial. Different combinations of chemotherapeutics are investigated in poly-chemotherapy studies: the CarboTax regimen (carboplatin plus paclitaxel), the GemTreo regimen (gemcitabine plus treosulfan), the DVP regimen (dacarbazine plus vindesin plus cisplatin), the BHD regimen (carmustine plus hyroxyurea plus dacarbazine), and the BOLD regimen (bleomycin plus vincristine plus lomustine plus darcarbazine). Furthermore, chemotherapy in combination with ipilimumab and the administration of specific BRAF, c-KIT, and N-RAS inhibitors to patients with mutations within the respective genes are being evaluated in clinical trials (S3-Leitlinie Melanom, 2013).

Colorectal Cancer (CRC)

Colorectal cancer (CRC) is one of the most common cancers in the world. Early detection and surgery with excision of the tumor are currently of critical importance for successful treatment. For localized tumors, i.e., tumors that have not evolved into a metastasizing disease, surgical intervention with radical resection of the tumor and surrounding bowel and tissues is performed. Colorectal tumors are categorized into several stages according to Dukes' stages A-D or more recently, according to the TNM classification. Early stage tumors (Dukes' stages A and B) are generally associated with a relatively favorable outcome, while later stage tumors, presenting with metastasis (Dukes' stage C and D) have poor survival rates. Unfortunately, metastasis often goes undetected until the tumor has grown to a considerable size. The tumor typically metastasizes to regional lymph nodes, but distant metastasis to the liver and lung are also common.

Patients with early-stage CRC (Stage I and II or Dukes' A and B) undergo surgical resection only and are not treated chemotherapeutically. Almost one-fourth of early-stage patients with non-metastatic disease, however, relapse with metastasis later, Patients diagnosed with metastatic forms of CRC, namely Dukes' C with lymph node metastasis and Dukes' D with hematological dissemination, have five-year survival rates of 37% and 11%, respectively. Patients diagnosed at an early stage (Dukes' A and B) with no evidence of metastatic disease at the time of surgery have a significantly better prognosis having five-year survival rates of 85% and 67%, respectively (Cancer Research UK, 2004). However, a significant proportion of these patients (10%-45%) relapse with metastatic disease.

Chemotherapy has proven effective for Dukes' stage C tumors. Newer studies also indicate the value of chemotherapy for some patients with early colorectal cancer at risk of metastatic relapse. However, although chemotherapeutic intervention has been implemented for some patients with early colon cancer, its implementation as a routine treatment is not cost effective and can be counterproductive. The side effects associated with the treatment make it desirable to avoid the use of chemotherapy except in cases of high relapse risk.

Ovarian/Endometrial Cancer

Ovarian cancer is among the most lethal gynecologic malignancies in developed countries. In the United States, approximately 23,000 women are diagnosed with the disease and almost 14,000 women die from it each year. There are three main types of ovarian cancer: epithelial, germ cell, and sex cord stromal. About 90% of ovarian cancers start in the epithelial tissue (the lining of the outside of the ovary). This type of ovarian cancer is divided into serous, mucinous, endometrioid, clear cell, transitional, and undifferentiated types. The risk of epithelial ovarian cancer increases with age, especially after the age of 50. Germ cell tumors account for about 5% of ovarian cancers. They begin in the egg-producing cells. This type of ovarian cancer can occur in women of any age, but about 80% are found in women under the age of 30. The main subtypes are teratoma, dysgerminoma, endodermal sinus tumor, and choriocarcinoma. Sex cord stromal tumors, about 5% of ovarian cancers, grow in the connective tissue of the ovary. Most are found in older women. Despite progress in cancer therapy, ovarian cancer mortality has remained virtually unchanged over the past two decades. Given the steep survival gradient relative to the stage at which the disease is diagnosed, early detection remains the most important factor in improving long-term survival of ovarian cancer patients.

Endometrial cancer is the most common gynecologic malignancy and accounts for about 13% of all malignancies occurring in women. There are about 34,000 cases of endometrial cancer diagnosed in the United States each year. All endometrial carcinomas arise from the glands of the lining of the uterus. Adenocarcinoma accounts for 75% of all endometrial carcinoma. Endometrial adenocarcinomas that contain benign or malignant squamous cells are known as adenocanthomas and adenosquamous carcinomas respectively and account for 30% of endometrial cancers. The remaining types of endometrial carcinoma have a poorer prognosis. About 3% have a clear cell carcinoma morphology, and about 1% have a papillary carcinoma morphology.

Ovarian cancer refers at least to a cancer which is one or more selected from the group consisting of serous ovarian cancer, mucinous ovarian cancer, endometrioid ovarian cancer, clear cell ovarian cancer, transitional ovarian cancer and/or undifferentiated ovarian cancer, teratoma, dysgerminoma, endodermal sinus tumor, and choriocarcinoma, endometrial cancer includes, endometrial carcinomas, adenocarcinoma, endometrial adenocarcinomas, adenocanthomas, adenosquamous carcinomas, clear cell carcinoma, and papillary carcinomas.

Breast Cancer

Breast cancer is a heterogeneous malignant disease exhibiting diverse biological characteristics and clinical responses. Gene expression profiling has defined genetic signatures corresponding to at least five distinct molecular subtypes of breast cancer, including an aggressive form known as triple-negative (TN) breast cancer.

There are three endogenous molecules that have been identified which promote many breast cancers: estrogen receptor (ER), progesterone receptor (PR), and human epidermal growth factor receptor 2 (HER2). By definition, Triple Negative (TN) breast cancer fails to express these three molecules. Although TN breast cancer represents a relatively small percentage of all breast cancers (about 20%), it is a typically high grade (poorly differentiated) and rapidly progressive, with a higher risk of relapse and lower survival than other subtypes of breast cancer. Therefore, TN breast cancer is associated with a disproportionate number of deaths. Additionally, for unknown reasons, TN breast cancer is often diagnosed in younger women and women of African-American descent. Women carrying mutant BRCA1 or BRCA 2 germline genes are at high risk for the development of both breast and ovarian cancer.

Current clinical approaches for breast cancer typically include agents that target the three molecules identified to promote many breast cancers, such as endocrine therapies and the monoclonal antibody trastuzumab targeting HER2. Because TN breast cancer is defined as the absence of these targets, conventional cytotoxic chemotherapy is currently the mainstay systemic treatment for patients with TN breast cancer. However, conventional systemic treatments are limited by the poor therapeutic response, high toxicity, and the development of resistance. Although new approaches in the treatment of TN breast cancer such as targeting DNA repair with PARP inhibitors have emerged, there have been relatively fewer therapeutic advances in TN breast cancer when compared to other subtypes of the disease. Thus, there is a pressing need for targeted approaches toward the treatment of TN breast cancer.

Bladder Cancer

Bladder cancer, also known as urothelial carcinoma (transitional cell carcinoma), is a type of cancer that is found in the lining of the urinary tract including the pelvis, ureters, bladder, and parts of the urethra. The most common form of bladder cancer is urothelial carcinoma. Bladder cancer occurs in people of all races and can affect people of any age. Bladder cancer is the fourth most common type of cancer in men and the ninth most common cancer in women. Bladder cancer is responsible for approximately 170,000 deaths per year in the United States.

While scientists do not know the exact cause(s) of bladder cancer, tobacco is believed to be the main known contributor. Occupational exposure in the workplace to carcinogens, such as benzidine (i.e., aromatic amines), can also result in bladder tumors. Occupations at risk for exposure to bezidine are bus drivers, rubber workers, motor mechanics, leather workers, blacksmiths, machine setters, mechanics, and hairdressers—because of the frequent exposure to permanent hair dyes. One other modifiable factor that is less strongly associated with bladder cancer is obesity.

Bladder cancer or urothelial carcinoma is often described based on how far they have invaded the wall of the bladder. Papillary carcinomas, or non-invasive bladder cancer, grow in slender, finger-like projections from the inner surface of the bladder toward the hollow center. Papillary tumors often grow toward the center of the bladder without growing into the deeper bladder layers. Low-grade (slow growing), non-invasive papillary cancer tends to have a good outcome. Flat carcinomas are another example of non-invasive bladder cancer. Flat carcinomas do not grow toward the hollow part of the bladder. If either a papillary or flat tumor grows into deeper layers of the bladder, it is called an invasive urothelial carcinoma. Invasive bladder cancers are more likely to spread and are much harder to treat.

Other cancers of the bladder are squamous cell carcinoma, adenocarcinoma, small cell carcinoma, and sarcoma.

Current treatment of bladder cancer involves invasive surgery, radical cystectomy, intravesical therapy, chemotherapy, radiation therapy and/or immunotherapy. However, these treatments are replete with drawbacks such as flu-like symptoms, extreme fatigue, hair-loss, DNA damage, development of secondary cancer, cell migration into the bloodstream, and complications from surgery.

Kidney Cancer

Kidney cancer (also referred to as renal cancer or renal cell carcinoma) mostly affects adults between 50 and 70 years of age. If detected early, kidney cancer is curable. However, symptoms may not appear until the tumor has grown to a large size or metastasized to other organs, at which point treatment is palliative.

In this disclosure, renal cancer and kidney cancer refer to renal cell carcinoma.

The 5-year survival rate for individuals diagnosed with kidney cancer is about 90% for those individuals whose tumor is confined to the kidney, about 60% if it has limited spread to nearby tissues, and about 9% if it has spread to distant sites (American Cancer Society, Detailed Guide: Kidney Cancer. "What Are the Key Statistics for Kidney Cancer (Renal Cell Carcinoma)?").

The majority of kidney cancers are renal cell carcinomas (which accounts for over 90% of malignant kidney tumors), also known as renal adenocarcinomas or clear cell carcinomas. There are five main types of renal cell carcinoma that are identified based on microscopic examination of cell type: clear cell, papillary, chromophobe, collecting duct, and "unclassified." Kidney cancers are also usually graded on a scale of 1 through 4 to indicate how similar the nuclei of the cancer cells are to the nuclei of normal kidney cells (grade 1 renal cell cancers have cell nuclei that differ very little from normal kidney cell nuclei and generally have a good prognosis, whereas grade 4 renal cell cancer nuclei appear as undifferentiated as distinguished from differentiated normal kidney cell nuclei and have a worse prognosis). In addition to grade, kidney cancers are also characterized by stage, which describes the size of cancer and degree of metastasis. The most commonly used staging system is that of the American Joint Committee on Cancer (AJCC) (also referred to as the TNM system), although the Robson classification is an older system that may be occasionally used.

Risk factors for kidney cancer include the following: age older than 50 years; male (men are twice as likely to get kidney cancer compared to women); cigarette smoking; exposure to asbestos, cadmium, or organic solvents; obesity; a high-fat diet; and von Hippel-Lindau disease (a genetic condition that has a high incidence of kidney cancer).

Symptoms of kidney cancer include hematuria (blood in the urine), abdominal or low back pain, weight loss, fatigue, anemia, fever, high blood pressure, and leg or ankle swelling.

In addition to a detailed medical history, physical examination, and laboratory blood testing, diagnosis of kidney cancer may typically include a computed tomography (CT) scan, ultrasound, magnetic resonance imaging (MRI), intravenous pyelography (a kidney test that utilizes dye and x-rays), or arteriography (a test in which dye is applied to the blood vessels feeding the kidney). To detect metastatic disease, chest X-ray and bone scan are commonly implemented.

Treatment of kidney cancer in individuals whose tumor is confined to the kidney may involve surgical removal of the kidney (nephrectomy) and surrounding tissue. Radiation therapy may be applied to treat pain and advanced or metastatic kidney cancers or to help shrink a tumor that is causing obstruction. Immunotherapy, such as interferon and interleukin-2, may be used to boost the immune system in patients with advanced kidney cancer (Journal of the American Medical Association, JAMA Patient Page: Kidney Cancer).

Lung Cancer

Lung cancer is the leading cause of cancer death in the United States. Lung cancer is categorized as either non-small cell lung carcinoma (NSCLC) or small cell lung carcinoma, with NSCLC representing more than 80% of cases. For the most common type of lung cancer, non-small cell lung cancer (NSCLC), the five-year survival rate is 70-80% for stage I disease without nodal or distant metastasis, but only 5-15% for advanced stage IV (distant) disease.

Current treatments for lung cancer include surgery, radiation, classical chemotherapeutic agents (platinum compounds, taxanes), and targeted therapies (inhibitors of VEGFR, EGFR, IGFR, HDACS, and the proteasome). However, despite advances in treatment, five-year survival rates are about 16%. Numerous clinical trials evaluating classical chemotherapy drugs for lung cancer indicate that a therapeutic plateau with current drugs may have been reached. Therefore, there is a need for new drugs for the treatment of lung cancer that have different mechanisms of action.

Checkpoint Inhibitors

One area of study on expanding the effect of immunotherapy drugs is the category of checkpoint inhibitors. Checkpoint inhibitors are antibody-based agents that mobilize the immune T-cell response. Checkpoint inhibitors block cancer cells' use of molecular switches known as checkpoints that normally prevent T cells from attacking healthy tissues. When these checkpoints, such as PD-1 (programmed death 1) and CTLA4 (cytotoxic T-lymphocyte-associated protein 4), are hijacked by cancer cells, the immune system's T-cell response is switched off, allowing the cells to multiply and the tumors to grow. Checkpoint inhibitors (anti-PD-1, anti-CTL4, and anti-PDL-1 (programmed death ligand 1 expressed on the surface of tumor cells)) flip the switch back on, freeing the immune response so that T cells are activated and destroy the cancer cells.

Checkpoint inhibitors work best against so-called hot tumors. Hot tumors are cancers that have been invaded by T cells and macrophages, creating an inflamed tumor. This response by the immune army hasn't killed the tumor, but because T cells are present within the tumor, they are more easily mobilized against the cancer. Checkpoint inhibitors release the inhibitions the tumor has clamped on the T cells. Once the T cells are free of inhibitions, they can freely kill the cancer cells.

Tumors can be classified as "hot" or "cold" depending on the functional capacity of cells within the tumor microenvironment to mount a cytotoxic immune response against the tumor. "Cold" tumors, by contrast, are cancers that, for various reasons, haven't been recognized or haven't provoked a strong tumor cytotoxic response by the immune system. Immune T cells may have been unable to penetrate the tumor microenvironment. The microenvironment in and around tumor cells comprises blood vessels, structural elements, and specialized immune cells; the latter include myeloid-derived suppressor cells and regulatory T cells (abbreviated as Tregs). These Tregs turn down the intensity of the normal immune response by secreting immunosuppressive chemical messengers like cytokines that impede the movement of cytotoxic T cells (T effector abbreviated as Teff) into the tumor resulting in the "immune desert" comprising a cold tumor.

Hot tumors in contrast are populated bt cytotoxic T-cells and often have a high mutational load. That is, they have many changes in their DNA code that cause the cancer cells to produce distinctive new proteins called "neoantigens" expressed on their cell surface. These neoantigens make the tumor more prone to recognition by the immune system, and thus more likely to provoke a strong immune response.

This immune desert is one of the limitations of current immunotherapy. There is a long felt need to effectively apply immunotherapy to cancers that are immunologically cold. In other words, how to make immunologically cold cancers immunoresponsive.

Current checkpoint inhibitor therapies, however, are effective at treating cancer in a relatively small population of cancer subject population, which is in part due to pre-existing immune activation and presence of the inhibitory receptors. Accordingly, there is a need to develop methods and combination therapies to initiate or enhance the effectiveness of the checkpoint inhibitors in both the nonresponding subject population and the responding subject population.

Anti-Tumor Immune Enhancer (ATIE) (e.g., AMPLIGEN)

This disclosure is directed in part to an Anti-Tumor Immune Enhancer (ATIE) which is also referred to in this disclosure as AMPLIGEN, rintatolimod, rugged RNA, a mismatched dsRNA or dsRNA. The Anti-Tumor Immune Enhancer (ATIE) enhancer has the properties described below.

One embodiment of AMPLIGEN is as follows: AMPLIGEN® (Poly I: Poly $C_{12}U$) is a synthetic double-stranded ribonucleic acid in which uridylic acid (U) substitution in the cytidylic chain creates a region of non-hydrogen bonding in the molecular configuration. The chemical name is polyriboinosinic: polyribocytidylic(12:1)uridylic acid. The USAN name for AMPLIGEN® is rintatolimod. AMPLIGEN® is a selective activator of Toll-like receptor 3 (TLR3) and exerts at least three interrelated activities (in vivo and in vitro): 1) immunomodulatory activity, 2) antiviral activity against RNA and DNA viruses, and 3) tumor cell antiproliferative (antineoplastic) activity.

Poly I: Poly $C_{12}U$ is a structural analog of the polyribonucleotide complex consisting of polyriboinosinic acid hydrogen-bonded with polyribocytidylic acid, Poly I: Poly C. In the Poly C strand, uridylic acid substitutions occur on an average of every 12 to 13 bases, producing a duplex Poly I: Poly $C_{12}U$, containing specifically configured regions interspersed with uninterrupted regions. The single-stranded RNA (ssRNA) raw materials, Poly I and Poly $C_{12}U$, are annealed under controlled conditions to form the double-stranded RNA (dsRNA) AMPLIGEN® (Poly I: Poly $C_{12}U$) molecules as shown in FIG. 1.

FIG. 1 depicts Poly I: Poly $C_{12}U$ subunit and the interaction of base pairs of Poly I and Poly $C_{12}U$. Single Inosine (blue) binds non-covalently to cytosine (green) but not with uridine (red). In this structure, Poly I (inosinic acid) is hydrogen-bonded (presented by:) to Poly C (cytidylic acid), with uridylic acid substitution occurring on an average of every 12 to 13 base pairs.

AMPLIGEN® (FIG. 1) has several chiral centers (the biochemical property of a molecule being nonsuperimposable on its mirror image) provided by both its primary and secondary structure. Chiral centers are found in the nucleotide bases, which form the two primary structures for each ssRNA chain of the Poly I: Poly $C_{12}U$ molecule. Additional chiral centers are formed by the association of each biologically inactive chain through hydrogen bonding of the complimentary bases into the biologically active Poly I: Poly $C_{12}U$ secondary structure. Hydrophobic bonding (π-π interactions) between adjacent bases of the dsRNA is a phenomenon known as base-stacking and produces a flexible, linear symmetrical helical secondary structure of defined size and shape. Perturbation of helicity results in the loss of the chiral centers characteristic of the secondary structure. The double-stranded configuration of Poly I: Poly $C_{12}U$ is destroyed when temperature or other external ionic forces exceed the strength of the hydrogen bonds that confer the non-covalent stabilization of the helix.

Another embodiment(s) of AMPLIGEN is a specific type of mismatched dsRNA as described as follows: The mismatched dsRNA may be of the general formula $rI_n \cdot r(C_{11-14}U)_n$, which is preferably $rI_n \cdot r(C_{12}U)_n$. The formula $rI_n \cdot r(C_{11-14}U)_n$ represents a double-stranded RNA with one strand being represented by $rI_n$ and the other strand represented by $(C_{11-14}U)_n$, wherein the dot symbol "·" represents that the two strands are hybridized to form a double-stranded RNA structure.

$rI_n$ represents polyriboinosine of n bases. "r" represents the RNA-like form of inosine which is riboinosine. This is as opposed to 2'-deoxyinosine. n represents the total length of this single-stranded inosine molecule—a single-stranded RNA.

$r(C_{11-14}U)_n$ represents a single-stranded RNA which comprises C bases and U bases with the ratio of C bases to U bases being for every 11-14 C there is a single U. n represent the total length of this single-stranded RNA.

$rI_n \cdot r(C_{11-14}U)_n$, therefore, represents a double-stranded RNA with $rI_n$ hybridized to $r(C_{11-14}U)_n$. Since n represents the length for both strands, both strands of ssRNA are the same length which gives rise to a dsRNA with no significant single-stranded regions in the middle or at the end of the double-stranded structure.

In this disclosure, absent indications otherwise, all the polynucleotides administered to a patient is RNA or chemical analogs thereof such as riboinosine (i.e., not DNA unless otherwise indicated). "n" is the length of the dsRNA (in bases) and n is an integer having a value of from 40 to 40,000. In this and the other formulae that follow r=ribo and rI=inosine.

Other mismatched dsRNAs for use in the present invention are based on co-polynucleotides selected from poly $(C_m,U)$ and poly $(C_m,G)$ in which m is an integer having a value of from 4 to 29 and are mismatched analogs of complexes of polyriboinosinic and polyribocytidilic acids, formed by modifying $rI_n \cdot rC_n$ to incorporate unpaired bases (uracil or guanine) within the polyribocytidylate $(rC_m)$ strand. Alternatively, the dsRNA may be derived from $r(I) \cdot r(C)$ dsRNA by modifying the ribosyl backbone of polyriboinosinic acid $(rI_n)$, e.g., by including 2'-O-methyl ribosyl residues. The mismatched dsRNA may be complexed with an RNA-stabilizing polymer such as lysine cellulose. Of these mismatched analogs of $rI_n \cdot rC_n$, the preferred ones are of the general formula $rI_n \cdot r(C_{11-14},U)_n$ or $rI_n \cdot r(C_{29},G)_n$, and are described by Ts'o & Carter in U.S. Pat. Nos. 4,024,222 and 4,130,641; the disclosures of which are hereby incorporated by reference. The dsRNAs described therein are generally suitable for use according to the present invention.

Other examples of mismatched dsRNAs for use in the invention include:

$rI_n \cdot r(C_4, U)$—ratio of C to U in one strand is 4:1;
$rI_n \cdot r(C_7, U)$—ratio of C to U in one strand is 7:1;
$rI_n \cdot r(C_{13}, U)$—ratio of C to U in one strand is 13:1;
$rI_n \cdot r(C_{22}, U)$—ratio of C to U in one strand is 22:1;
$rI_n \cdot r(C_{20}, G)$—ratio of C to G in one strand is 20:1;
$rI_n \cdot ribo(C_{4-29}U)_n$—ratio of C to U in one strand is 4-29:1;
$rI_n \cdot r(C_{11-14}U)_n$—ratio of C to U in one strand is 11-14:1;
$rI_n \cdot ribo(C_{12}U)_n$—ratio of C to U in one strand is 12:1;
$rI_n \cdot r(C_{29},G)_n$—ratio of C to U in one strand is 29:1;
$rI_n \cdot ribo(C_{30}U)_n$—ratio of C to U in one strand is 30:1;
$rI_n \cdot ribo(C_{30-35}U)_n$—ratio of C to U in one strand is 30-35:1; and
$r(Poly\ A \cdot Poly\ U)_n$.

Briefly, AMPLIGEN is dsRNA. It is understood that if one strand is n in length the other strand will also be n in length even if it is not stated. Also, each intermediate value of the ratio is also claimed where a range is claimed.

For example, $rI_n \cdot ribo(C_{4-29}U)_n$ will encompass individually: $rI_n \cdot ribo(C_4U)_n$, $rI_n \cdot ribo(C_5U)_n$, $rI_n \cdot ribo(C_6U)_n$, $rI_n \cdot ribo(C_7U)_n$, $rI_n \cdot ribo(C_8U)_n$, $rI_n \cdot ribo(C_9U)_n$, $rI_n \cdot ribo(C_{10}U)_n$, $rI_n \cdot ribo(C_{11}U)_n$, $rI_n \cdot ribo(C_{12}U)_n$, $rI_n \cdot ribo(C_{13}U)_n$, $rI_n \cdot ribo(C_{14}U)_n$, $rI_n \cdot ribo(C_{15}U)_n$, $rI_n \cdot ribo(C_{16}U)_n$, $rI_n \cdot ribo(C_{17}U)_n$, $rI_n \cdot ribo(C_{18}U)_n$, $rI_n \cdot ribo(C_{19}U)_n$, $rI_n \cdot ribo(C_{20}U)_n$, $rI_n \cdot ribo(C_{21}U)_n$, $rI_n \cdot ribo(C_{22}U)_n$, $rI_n \cdot ribo(C_{23}U)_n$, $rI_n \cdot ribo(C_{24}U)_n$, $rI_n \cdot ribo(C_{25}U)_n$, $rI_n \cdot ribo(C_{26}U)_n$, $rI_n \cdot ribo(C_{27}U)_n$, $rI_n \cdot ribo(C_{28}U)_n$, and $rI_n \cdot ribo(C_{29}U)_n$.

As another example, $rI_n \cdot ribo(C_{30-35}U)_n$ will encompass individually: $rI_n \cdot ribo(C_{30}U)_n$, $rI_n \cdot ribo(C_{31}U)_n$, $rI_n \cdot ribo(C_{32}U)_n$, $rI_n \cdot ribo(C_{33}U)_n$, $rI_n \cdot ribo(C_{34}U)_n$, and $rI_n \cdot ribo(C_{35}U)_n$.

That is, each of the above molecules is also individually claimed as part of the invention and individually viewed as an embodiment.

For a subject (e.g., 150 lb human) the dose of dsRNA may range from 0.1 to 25,000 µg, preferably from 0.5 to 5,000 µg.

Alternatively, the dsRNA may be matched (i.e., not in mismatched form). Thus polyadenylic acid complexed with polyuridylic acid (poly A·poly U) may also be used. The mismatched or matched dsRNA may be administered intravenously, intramuscularly, intranasally, or topically.

Formulations for administration include aqueous solutions, syrups, elixirs, powders, granules, tablets and capsules which typically contain conventional excipients such as binding agents, fillers, lubricants, disintegrants, wetting agents, suspending agents, emulsifying agents, preservatives, buffer salts, flavoring, coloring and/or sweetening agents. They may be applied nasally with a spray or nebulizer. It will be appreciated that the preferred route will vary with the condition and age of the recipient, the nature of the infection, and the chosen active ingredient.

In another aspect, the mismatched dsRNA (AMPLIGEN) can be a rugged dsRNA. Specifically-configured dsRNA may be of the general formula $ribo(I_n) \cdot ribo(C_{4-29}U)_n$, $ribo(I_n) \cdot ribo(C_{11-14}U)_n$, or $ribo(I_n) \cdot ribo(C_{12}U)_n$, wherein the strands are comprised of ribonucleotides (ribo) and n is an integer from about 40 to about 40,000. For example, a strand comprised of poly(ribocytosinic$_{4-29}$ribouracilic acid), poly(ribocytosinic$_{11-14}$ribouracilic acid), or poly(ribocytosinic$_{12}$ribouracilic acid) may be partially hybridized to an opposite strand comprised of poly(riboinosinic acid) such that the two strands form an RNA double helix that is not paired at the uracil base (i.e., mismatch).

After synthesis, rugged dsRNA may be isolated by at least subjecting the partially hybridized strands of a population of dsRNA to conditions that denature most dsRNA (more than 50 mol %, at least 80 mol %, at least 90 mol %, at least 95 mol %, or at least 98 mol %) in the population, and then selection negatively or positively (or both) for dsRNA that remain partially hybridized. The purity of rugged dsRNA may thus be increased from less than about 0.1-10 mol % (e.g., less than about 5 mol %) relative to all RNA in the population after synthesis. It is preferred that the rugged dsRNA be more than about 80-98 mol % relative to all RNA present in the same mixture with the rugged dsRNA (at least 80 mol %, at least 90 mol %, at least 95 mol %, or at least 98 mol %) after selection. The denaturing conditions to unfold at least partially hybridized strands of dsRNA may comprise an appropriate choice of buffer salts, pH, solvent, temperature, or any combination thereof. Conditions may be empirically determined by observation of the unfolding or melting of the duplex strands of ribonucleic acid. The yield of rugged dsRNA may be improved by partial hydrolysis of longer strands of ribonucleic acid, then selection of (partially) hybridized stands of appropriate size and resistance to denaturation.

The molecular weight of rugged dsRNA may be from about 250 kDa to about 320 kDa, or from about 270 kDa to about 300 kDa. Lengths of a single or both strands of rugged dsRNA may be from about 380 bases to about 450 bases, or from about 400 bases to about 430 bases. The number of helical turns made by duplexed RNA strands of rugged dsRNA may be from about 30 to about 38, or from about 32 to about 36.

In another aspect, at least one or more different rugged dsRNA may be administered to a subject (e.g., human patient or animal) in need of such treatment.

The recommended dosage of mismatched dsRNA will depend on the clinical status of the subject and the physician's or veterinarian's experience treating the disease or other pathological condition. Mismatched dsRNA may be dosed at from about 0.5 mg to about 60 mg, from about 5 mg to about 40 mg, or from about 10 mg to about 20 mg in a subject (e.g., body mass of about 70-80 Kg for a human patient) on a schedule of either once a day up to 7 days weekly or once weekly to thrice weekly (preferably twice weekly), albeit the dose amount and/or frequency may be varied by the physician or veterinarian in response to the subject's symptoms. The nucleic acid in solid form may be dissolved in physiological phosphate-buffered saline or sterile water (WFI), and then infused intravenously. It will be appreciated that the preferred dosage may vary with the age, condition, gender, or health status of the subject; the nature of the disease or other pathological condition, including the number and severity of symptoms; and the chosen active ingredient.

AMPLIGEN® (rintatolimod) is an optimized TLR3 agonist and endogenous interferon (rFN) inducer in late-stage clinical development with the ability to augment both innate and acquired immunity including cellular responses (T-cells) in humans with immunodeficiency (HIV disease) (Thompson et al, 1996), as well as NK cells and humoral (B-cells) responses in normal human volunteers (Overton et al., 2014; Zarling et al., 1980; Strayer et al., 2015).

For this disclosure, AMPLIGEN may refer to any dsRNA disclosed. Also, AMPLIGEN may refer to any dsRNA disclosed except for (Poly A·Poly U)$_n$.

Immune Checkpoints and Checkpoint Inhibitors (Also Called Immune Checkpoint Inhibitors)

Immune checkpoints, which act as the off-switch on the T-cells of the immune system, have been investigated to restore the immune response with targeted agents, thus indirectly treating cancer by activating the body's immune system. As used herein, the terms "checkpoint inhibitor" and "immune checkpoint inhibitor" are interchangeable and refer to molecules that totally or partially (1) reduce, (2) inhibit, (3) interfere with (4) modulate or (5) any combination of (1) to (4), one or more checkpoint proteins. Checkpoint proteins regulate T-cell activation or function. These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies. In some aspects of this and other embodiments the immune checkpoint inhibitor is selected from a group consisting of an anti-PD-1 antibody, an anti-PD-L1 antibody, an anti-PD-L2 antibody, an anti-CTLA-4 antibody, and combinations thereof. Preferably, the immune checkpoint inhibitor is selected from a group consisting of alemtuzumab (CAMPATH-1H®); AMP-224 (GlaxoSmithKline/Amplimmune), AMP-514 (Amplimmune/AZ), arelumab (Merck Serono), atezolizumab (TECENTRIQ®; Roche/Genentech); AUNP 12 (Aurigene and Pierre Fabre), avelumab (BAVENCIO®); BMS-936559 BMS-986016 (Bristol-Meyers Squibb), BMS-986016 (Bristol-Meyers Squibb); cemiplimab)(LIBTAYO®); CP-870,893 (Genentech), CT-011, durvalumab (IMFINIZI®); Galiximab (Biogen Idec), IMP321 (Immutep S.A.), INCB024360 (Incyte) Indoximod (NewLink Genetics), IPH2101 (Innate Pharma/Bristol-Myers Squibb), ipilimumab (YERVOY®, (Bristol- Myers Squibb), lambrolizumab, lirilumab (Bristol-Myers Squibb), MDX-1105 (Medarex, Inc./Bristol Myer Squibb), MEDI-4736 (Medimmune/AstraZeneca), MEDI-6469 (MedImmune/AZ), MGA271 (Macrogenics), MIHI; Mogamulizumab (Kyowa Hakko Kirin), MPDL3280A (Roche), nivolumab (OPDIVO®, Bristol-Myers Squibb), NLG-919 (NewLink Genetics), ofatumumab (ARZERRA®); pembrolizumab (KEYTRUDA®; Merck); PF-05082566 (Pfizer), pidilizumab (Curetech), rituximab (RITUXAV); tremelimumab (formerly ticilimumab; CP-675;206); urelumab (Bristol-Meyers Squibb), Varlilumab (CellDex Therapeutics), and any combinations thereof.

Aspects of immune checkpoints are known and were published in the following: U.S. Pat. Nos. 8,168,757; 8,735,553; WO2002086083; WO2004004771; WO2004056875; WO2006121168; WO2008156712; WO2010077634; WO2011066389; WO2011161699; WO2012168944; WO2013132317; WO2013144704; WO2014055897; WO2014100079; WO2016044900; WO2016142833; WO2016142835; WO2016142852; WO2016142886; and WO2016142894.

Recently, ipilimumab (Yervoy), a monoclonal antibody that targets cytotoxic T-lymphocyte-associated antigen 4 (CTLA-4) and nivolumab (Opdivo), a monoclonal antibody that targets the programmed cell death protein 1 (PD-1) on the surface of T-cells, have been approved by the U.S. Food and Drug Administration for the treatment of advanced melanoma, advanced renal cell carcinoma, and non-small cell lung cancer.

Examples of immune checkpoint inhibitors include a reagent that inhibits or interacts with a ligand of a checkpoint protein. A partial list of checkpoint proteins are listed below: 2B4; A2aR; B-7 family ligand; B7-H3; B7-H4; B and T lymphocyte attenuator (BTLA); BMA; CD112; CD137; CD160; CD2; CD20; CD226; CD27; CD276; CD28; CD30; CD33; CD40; CD47; CD52; CD70; CD80; CD86; CGEN-15049; CHK 1; CHK2; cytotoxic T-lymphocyte antigen-4 (CTLA-4); DR3; galectin 9 (GALS); GITR; herpesvirus entry mediator (HVEM); HVEM; ICOS; IDO1; IDO2; Killer-Cell Immunoglobulin-Like Receptor (KIR); LAG3; LAIR; LAIR1; LAIR2; LIGHT; lymphocyte activation gene 3 (LAG-3); MARCO; OX-40; PD-1; PD-L1; PD-L2; PS; SIRP alpha; SLAM; T cell immunoreceptor with Ig and ITIM domains (TIGIT); T cell membrane protein 3 (TIM3); V-domain immunoglobulin (Ig)-containing suppressor of T-cell activation (VISTA); VTCN1; and any combination thereof.

PD-L1

PD-L1 is a negative regulator of immune activation through inhibition of effective T cell function. The co-inhibitory receptor programmed death 1 (PD-1), and its ligands are key regulators in a wide spectrum of immune responses and play a critical role in autoimmunity and self-tolerance as well as in cancer immunology. Emerging evidence suggests that cancer cells use the PD-1/PD-ligand (PDL) pathway to escape anti-tumor immunity. Based on this evidence, early phase human clinical trials targeting the PD-1/PDL pathway are currently underway for multiple human cancers. An anti-PD-L1 antibody is in phase II development for metastatic bladder cancer (Powles et al., MPDL3280A (anti-PD-L1) treatment leads to clinical activity in metastatic bladder cancer, Nature. 2014 Nov. 27; 515 (7528):558-62. doi: 10.1038/nature13904.; Errico A., Immunotherapy: PD-1-PD-L1 axis: efficient checkpoint blockade against cancer, Nat Rev Clin Oncol. 2015 February; 12(2):63. doi: 10.1038/nrclinonc.2014.221. Epub 2014 Dec. 23.; Muenst S et al., The PD-1/PD-L1 pathway: biological background and clinical relevance of an emerging treatment target in immunotherapy., Expert Opin Ther Targets., 2015 February; 19(2):201-11. doi: 10.1517/14728222.2014.980235., Epub 2014 Dec. 10; M. S. Soloway. Intravesical and systemic chemotherapy in the management of superficial bladder cancer. Urol. Clin. North Am. 11 (4):623-635, 1984).

PD-L1 Inhibitor

The term "PD-L1 inhibitor" refers to a moiety (e.g., compound, nucleic acid, polypeptide, antibody) that decreases, inhibits, blocks, abrogates or interferes with the activity, binding of PD-L1 to its receptor, PD-1, or expression of PD-L1 (e.g., Programmed Cell Death 1 Ligand; PD-L1 (CD274); GI: 30088843), including variants, isoforms, species homologs of human PD-L1 (e.g., mouse) and analogs that have at least one common epitope with PD-L1. A PD-L1 inhibitor includes molecules and macromolecules such as, for example, compounds (small molecule compounds), nucleic acids, polypeptides, antibodies, peptibodies, diabodies, minibodies, single-chain variable fragments (ScFv), and fragments or variants thereof. Thus, a PD-L1 inhibitor as used herein, refers to any moiety that antagonizes PD-L1 activity, its binding to PD-1, or its expression. PD-L1 inhibitor efficacy can be measured, for example, by its inhibitor concentration at 50% (half-maximal inhibitor concentration or IC.sub.50). PD-L1 inhibitors include exemplary compounds and compositions described herein. A PD-L1 inhibitor antibody refers to a PD-L1 inhibitor which is a monoclonal or polyclonal antibody as described herein.

Pharmaceutical Composition

The pharmaceutical composition comprising one or more active agents listed above may be administered to a subject by any local or systemic route known in the art including enteral (e.g., oral, feeding tube, enema), topical (e.g., device such as a nebulizer for inhalation through the respiratory system, skin patch acting epicutaneously or transdermally, suppository acting in the rectum or vagina), and parenteral (e.g., subcutaneous, intravenous, intramuscular, intradermal, or intraperitoneal injection; buccal, sublingual, or transmucosal; inhalation or instillation intra-nasally or intratracheally). The pharmaceutical composition and/or the active agents may be micronized by milling or grinding solid material, dissolved in a vehicle (e.g., sterile buffered saline or water) for injection or instillation (e.g., spray), topically applied, or encapsulated in a liposome or other carrier for targeted delivery. It will be appreciated that the preferred route may vary with the age, condition, gender, or health status of the subject; the nature of the disease or other pathological condition, including the number and severity of symptoms; and the chosen active ingredient.

Formulation

Formulations for administration (i.e., pharmaceutical compositions) may include aqueous solutions, syrups, elixirs, powders, granules, tablets, and capsules which typically contain conventional excipients such as binding agents, fillers, lubricants, disintegrants, wetting agents, suspending agents, emulsifying agents, preservatives, buffer salts, flavoring, coloring, and/or sweetening agents. It will be appreciated that the preferred formulation may vary with the age, condition, gender, or health status of the subject; the nature of the disease or other pathological condition, including the number and severity of symptoms; and the chosen active ingredient.

Medicament Definition

In another aspect, a medicament (e.g., a pharmaceutical composition) containing the immune activator(s) is provided. Optional other components of the medicament include excipients and a vehicle (e.g., aqueous buffer or water for injection) packaged aseptically in one or more separate containers (e.g., nasal applicator or injection vial). Processes for using and making the medicament are also provided. Further aspects will be apparent from the following description and claims, and any generalizations thereto.

Effective Amount

The compositions are delivered in effective amounts. The term "effective amount" refers to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. Also, based on testing, the toxicity of the inhibitor is expected to be low. The effective amount for any particular application can vary depending on such factors as the disease or condition being treated, the particular inhibitor being administered, the size of the subject, or the severity of the disease or condition. One of ordinary skill in the art can empirically determine the effective amount of a particular active ingredient without necessitating undue experimentation. It is preferred generally that a maximum dose be used, that is, the highest safe dose according to medical judgment.

For any compound described herein, the therapeutically effective amount can be initially determined from preliminary in vitro studies and/or animal models. A therapeutically effective dose can also be determined from human data for inhibitors which have been tested in humans and for compounds which are known to exhibit similar pharmacological activities, such as other related active agents. The applied dose can be adjusted based on the relative bioavailability and potency of the administered compound. Adjusting the dose to achieve maximal efficacy based on the methods described above and other methods are well known in the art, is well within the capabilities of the ordinarily skilled artisan.

Administration

Suitable administration/treatment protocols for treating cancer or tumor in a subject include, for example, administering to the patient (subject) an effective amount of AMPLIGEN and an immune checkpoint inhibitor.

In some embodiments, the combination therapy of the invention comprises administration of AMPLIGEN and an immune checkpoint inhibitor. Any compound or chemical or formulation in this disclosure may be administered by any of the administration methods disclosed. The AMPLIGEN and the immune checkpoint inhibitor may be administered in any suitable manner known in the art. For example, the AMPLIGEN and the immune checkpoint inhibitor may be administered sequentially (at different times) or concurrently (at the same time).

In some embodiments, the immune checkpoint inhibitor is administered before administration of the AMPLIGEN. In some embodiments, the immune checkpoint inhibitor is administered simultaneously with the administration of the AMPLIGEN. In some embodiments, the immune checkpoint inhibitor is administered after administration of the AMPLIGEN.

In some embodiments, the AMPLIGEN or an immune checkpoint inhibitor is administered continuously. In some embodiments, the AMPLIGEN or immune checkpoint inhibitor is administered intermittently.

In some embodiments, the immune checkpoint inhibitor and the AMPLIGEN is co-administered, for example, the administration of said immune checkpoint inhibitor and the AMPLIGEN as two separate formulations. The co-administration can be simultaneous or sequential in either order. In one further embodiment, there is a time period while both (or all) antibodies simultaneously exert their biological activities. Said immune checkpoint inhibitor and AMPLIGEN are co-administered either simultaneously or sequentially for example, intravenous (i.v.) through a continuous infusion. When both therapeutic agents are co-administered sequentially the therapeutic agents are administered in two separate administrations that are separated by a "specific period of time". The term specific period of time is meant anywhere from 1 hour to 30 days. For example, one of the agents can be administered within the following time periods. About 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 day. About 24, 23, 22, 21, 20, 19, 18, 17, 16, 15, 14, 13, 12, 11, 10, 9, 8, 7, 6, 5, 4, 3, 2 or 1 hour. These are times from the administration of the other therapeutic agent. In some embodiments, the specific period time is 10, 9, 8, 7, 6, 5, 4, 3, 2, or 1 day. In other embodiment the time period is 24, 23, 22, 21, 20, 19, 18, 17, 16, 15, 14, 13, 12, 11, 10, 9, 8, 7, 6, 5, 4, 3, 2 or 1 hour. In some embodiments, simultaneous administration means at the same time or within a short period of time, usually less than 1 hour.

A dosing period as used herein is meant for a period of time, during which each member of the composition has been administered at least once. A dosing period is usually about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, and, in one embodiment, 6, 7, 8, 9, 10, 11, 12, 13, or 14 days, for example, 7 or 14 days.

In certain embodiments, multiple (for example, 2, 3, 4, 5, 6, 7, 8, 9, 10 or more) doses of an AMPLIGEN and multiple (for example, 2, 3, 4, 5, 6, 7, 8, 9, 10 or more) doses of an immune checkpoint inhibitor are administered to a subject in need of treatment.

In certain embodiments, the immune checkpoint inhibitor is administered in a dose of 0.01 mg/kg, 0.05 mg/kg, 0.1 mg/kg, 0.2 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg or 30 mg/kg. The dose of the immune checkpoint inhibitor may vary from about 0.01 mg/kg to 30 mg/kg, preferably 0.1 mg/kg to 20 mg/kg, more preferably 1 mg/kg to 10 mg/kg. In certain embodiments, the immune checkpoint inhibitor is administered by injection (e.g., subcutaneously or intravenously) at a dose of about 0.01 mg/kg to 30 mg/kg, e.g., about 0.1 mg/kg to 20 mg/kg, about 1 mg/kg to 10 mg/kg, about 1 mg/kg to 5 mg/kg., or about 1 to 3 mg/kg.

In certain embodiments, the checkpoint inhibitor is administered one dose per day, one dose every 2 days, one dose every 3 days, one dose every 4 days, one dose every 5 days, once a week, once every two weeks, once every three weeks or once every four weeks, preferably one dose every 3 days. In certain embodiments, the checkpoint inhibitor is administered as a single dose, in two doses, in three doses, in four doses, in five doses, or in 6 or more doses. The dosing schedule can vary from, e.g., once a week to once every 2, 3, or 4 weeks. In one embodiment, the immune checkpoint inhibitor is administered at a dose from about 1 mg/kg to 10 mg/kg every other week.

In certain embodiments, the AMPLIGEN is administered in a dose of 0.1 mg/kg, 0.2 mg/kg, 0.3 mg/kg, 0.5 mg/kg, 0.7 mg/kg, 0.8 mg/kg, 1 mg/kg, 2 mg/kg, 2.1 mg/kg, 3 mg/kg, 4 mg/kg, 5 mg/kg, 6 mg/kg, 7 mg/kg, 8 mg/kg, 9 mg/kg, 10 mg/kg, 15 mg/kg or 20 mg/kg. In another embodiment, the dosage of an AMPLIGEN of the invention administered to prevent and/or treat a cancer associated with increased levels of AMPLIGEN in a patient is a unit dose of about 0.1 mg/kg to about 20 mg/kg, about 0.1 mg/kg to about 10 mg/kg, about 0.1 mg/kg to about 8 mg/kg, about 0.1 mg/kg to about 7 mg/kg, about 0.1 mg/kg to about 6 mg/kg, about 0.1 mg/kg to about 5 mg/kg, about 0.1 mg/kg to about 4 mg/kg, preferably, about 0.1 mg/kg to about 3 mg/kg, about 0.2 mg/kg to 3 mg/kg, about 0.3 mg/kg to about 3 mg/kg, about 0.4 mg/kg to about 3 mg/kg, about 0.6 mg/kg to about 3 mg/kg, about 0.8 mg/kg to about 3 mg/kg, about 0.1 mg/kg to 2 mg/kg, about 0.1 mg/kg to 1 mg/kg. Total daily dose may vary from 20 mg to 200 mg, preferably 50 mg to 150 mg, most preferably 80 mg to 140 mg. In a preferred embodiment, an AMPLIGEN of the present invention is administered at a unit dose of about 0.1 mg/kg, about 0.2 mg/kg, about 0.4 mg/kg, about 0.6 mg/kg, about 0.8 mg/kg, about 1 mg/kg, about 2 mg/kg, about 3 mg/kg, about 4 mg/kg or 5 mg/kg. In one embodiment, the AMPLIGEN is administered at a dose from about 1 mg/kg to 10 mg/kg biweekly.

In certain embodiments, the AMPLIGEN is administered one dose per day, one dose every 2 days, one dose every 3 days, one dose every 4 days, one dose every 5 days, once a week, once every two weeks, or once every four weeks, preferably one dose every 3 days. In certain embodiments, the AMPLIGEN is administered as a single dose, in two doses, in three doses, in four doses, in five doses, or in 6 or more doses. The dosing schedule can vary from, e.g., once a week to once every 2, 3, or 4 weeks. In one embodiment, the AMPLIGEN is administered at a dose from about 0.50 mg/kg to 10 mg/kg every other week. In certain embodiments, the dose frequency may vary from once a day to once a month.

An effective amount of the AMPLIGEN and the immune checkpoint inhibitor may be administered for prevention or treatment of cancer. The appropriate dosage of the AMPLIGEN and/or the immune checkpoint inhibitor may be determined based on the type of disease to be treated, the type of the AMPLIGEN and the immune checkpoint inhibitor, the severity and course of the disease, the clinical condition of the subject, the subject's clinical history and response to the treatment, the symptoms involved, the subject's body mass, gender, immune status and the discretion of the attending physician. Suitable regimens can be selected by one skilled in the art by considering such factors and by following, for example, dosages reported in literature and recommended in the Physician's Desk Reference (59th ed., 2005).

Preferably, the dosages of therapeutic agents used in combination therapies of the invention are lower than those which have been or are currently being used to prevent and/or treat a tumor associated with increased levels of AMPLIGEN and/or immune checkpoint molecule.

In some embodiments, a method of treating cancer will be performed even with a low likelihood of success, but which, given the medical history and estimated survival expectancy of a patient, is nevertheless deemed to induce an overall beneficial course of action.

Accordingly, in one embodiment, the dose of the AMPLIGEN and immune checkpoint inhibitor is calculated as mg/kg body weight. However, in another embodiment, the dose of the AMPLIGEN and/or immune checkpoint inhibitor is a flat fixed dose that is fixed irrespective of the weight of the patient.

The AMPLIGEN and the immune checkpoint inhibitor may be administered by the same route of administration or by different routes of administration. In some embodiments, the AMPLIGEN is administered intravenously, intramuscularly, subcutaneously, topically, orally, transdermally, intraperitoneally, intraorbitally, by implantation, by inhalation, intrathecally, intraventricularly, or intranasally. In some embodiments, the immune checkpoint inhibitor is administered intravenously, intramuscularly, subcutaneously, topically, orally, transdermally, intraperitoneally, intraorbitally, by implantation, by inhalation, intrathecally, intraventricularly, or intranasally.

In some embodiments, the immune checkpoint inhibitor is a PD-L1 antagonist (for example, anti-PD-L1 antibody). In some embodiments, the anti-PD-L1 antibody is administered to the subject intravenously at a dose of 120 mg once every three weeks. In some embodiments, the anti-PD-L1 antibody is administered with an AMPLIGEN (for example, AMPLIGEN).

Antibody

An "antibody" may be a natural or conventional antibody in which two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE, having heavy chains designated alpha, delta, epsilon, gamma and mu, respectively.

The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site.

The light and heavy chains of an immunoglobulin each have three CDRs, designated CDR1-L, CDR2-L, CDR3-L and CDR1-H, CDR2-H, CDR3-H, respectively. A conventional antibody-antigen-binding site, therefore, includes six CDRs, comprising the CDR set from each of a heavy and a light chain V region.

"Framework Regions" (FRs) refer to amino acid sequences interposed between CDRs, i.e., to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively.

As used herein, a "human framework region" is a framework region that is substantially identical (about 85%, or more, in particular 90%, 95%, 97%, 99% or 100%) to the framework region of a naturally occurring human antibody.

As used herein, the term "antibody" denotes conventional antibodies and fragments thereof, as well as single domain antibodies and fragments thereof, in particular, variable heavy chain of single domain antibodies, and chimeric, humanized, bispecific or multispecific antibodies.

As used herein, antibody or immunoglobulin also includes "single domain antibodies" which have been more recently described and which are antibodies whose complementary determining regions are part of a single domain polypeptide. Examples of single domain antibodies include heavy chain antibodies, antibodies naturally devoid of light chains, single domain antibodies derived from conventional four-chain antibodies, engineered single domain antibodies. Single domain antibodies may be derived from any species including, but not limited to mouse, human, camel, llama, goat, rabbit and bovine. Single domain antibodies may be naturally occurring single domain antibodies known as heavy chain antibody devoid of light chains. In particular, Camelidae species, for example, camel, dromedary, llama, alpaca and guanaco, produce heavy chain antibodies naturally devoid of light chain. Camelid heavy chain antibodies also lack the CH1 domain.

The variable heavy chain of these single domain antibodies devoid of light chains are known in the art as "VHH" or "nanobody." Similar to conventional VH domains, VHHs contain four FRs and three CDRs. Nanobodies have advantages over conventional antibodies: they are about ten times smaller than IgG molecules, and as a consequence properly folded functional nanobodies can be produced by in vitro expression while achieving high yield. Furthermore, nanobodies are very stable, and resistant to the action of proteases. The properties and production of nanobodies have been reviewed by Harmsen and De Haard H J (Appl. Microbiol. Biotechnol. 2007 November; 77(1): 13-22).

The antibody of the invention may be a polyclonal antibody or a monoclonal antibody. Said monoclonal antibody may be humanized. In another example the antibody may be a fragment selected from the group consisting of Fv, Fab, F(ab')2, Fab', dsFv, (dsFv)2, scFv, sc(Fv)2, diabodies and VHH.

The term "monoclonal antibody" or "mAb" as used herein refers to an antibody molecule of a single amino acid composition that is directed against a specific antigen, and is not to be construed as requiring production of the antibody by any particular method. A monoclonal antibody may be produced by a single clone of B cells or hybridoma, but may also be recombinant, i.e. produced by protein engineering.

The term "chimeric antibody" refers to an engineered antibody which in its broadest sense contains one or more regions from one antibody and one or more regions from one or more other antibody(ies). In particular, a chimeric antibody comprises a VH domain and a VL domain of an antibody derived from a non-human animal, in association with a CH domain and a CL domain of another antibody, in particular a human antibody. As the non-human animal, any animal such as mouse, rat, hamster, rabbit or the like can be used. A chimeric antibody may also denote a multispecific antibody having specificity for at least two different antigens. In an embodiment, a chimeric antibody has variable domains of mouse origin and constant domains of human origin.

The term "humanized antibody" refers to an antibody which is initially wholly or partially of non-human origin and which has been modified to replace certain amino acids, in particular in the framework regions of the heavy and light chains, in order to avoid or minimize an immune response in humans. The constant domains of a humanized antibody are most of the time human CH and CL domains. In an embodiment, a humanized antibody has constant domains of human origin.

"Fragments" of antibodies comprise a portion of an intact antibody, in particular the antigen binding region or variable region of the intact antibody. Examples of antibody fragments include Fv, Fab, F(ab')2, Fab', dsFv, (dsFv)2, scFv, sc(Fv)2, diabodies, bispecific and multispecific antibodies formed from antibody fragments. A fragment of an antibody may also be a single domain antibody, such as a heavy chain antibody or VHH.

The term "Fab" denotes an antibody fragment having a molecular weight of about 50,000 Da and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 Da and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 Da and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, in particular by using gene recombination techniques. Divalent and multivalent antibody fragments can form either spontaneously by association of monovalent scFvs, or can be generated by coupling monovalent scFvs by a peptide linker, such as divalent sc(Fv).sub.2. "dsFv" is a VH::VL heterodimer stabilised by a disulphide bond.

"(dsFv)2" denotes two dsFv coupled by a peptide linker.

The term "bispecific antibody" or "BsAb" denotes an antibody which combines the antigen-binding sites of two antibodies within a single molecule. Thus, BsAbs are able to bind two different antigens simultaneously. Genetic engineering has been used with increasing frequency to design, modify, and produce antibodies or antibody derivatives with a desired set of binding properties and effector functions as described for instance in EP 2 050 764 A1.

The term "multispecific antibody" denotes an antibody which combines the antigen-binding sites of two or more antibodies within a single molecule.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Typically, antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with the relevant antigenic forms. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

This invention provides in certain embodiments compositions and methods that include humanized forms of antibodies. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may be used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgGl, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., I. Mol. Biol. 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

In one embodiment, the antibody of the invention is modified to reduce or inhibit the ability of the antibody to mediate antibody dependent cellular cytotoxicity (ADCC) and/or complement dependent cytotoxicity (CDC) functionality (i.e. an antibody with reduced Fc-effector function"). In particular, the antibodies of the present invention have no Fc portion or have an Fc portion that does not bind FcγRI and C1q. In one embodiment, the Fc portion of the antibody does not bind FcγRI, C1q, or FcγRIII. Antibodies with such functionality, in general, are known. There are native such antibodies, such as antibodies with an IgG4 Fc region. There also are antibodies with Fc portions genetically or chemically altered to eliminate the Antibody dependent cell cytotoxicity (ADCC) and/or complement dependent cytotoxicity (CDC) functionality.

Treat

The terms "treat", "treating", "treated" or "treatment", as used herein, refer to therapeutic treatment wherein the object is to eliminate or lessen symptoms. Beneficial or desired clinical results include, but are not limited to, elimination of symptoms, alleviation of symptoms, diminishment of extent of condition, stabilized (i.e., not worsening) state of condition, delay or slowing of progression of the condition.

Cancer

As used herein and unless otherwise defined, "cancer" refers to the growth, division or proliferation of abnormal cells in the body. Cancers that can be treated with the combinations, pharmaceutical compositions, products and methods described herein include, but are not limited to all of the cancers described in this disclosure.

Synergy

As used herein, the term "synergy" or "synergistic effect" when used in connection with a description of the efficacy of a combination of agents, means any measured effect of the combination which is greater than the effect predicted from a sum of the effects of the individual agents.

Additive Effect

As used herein, the term "additive" or "additive effect" when used in connection with a description of the efficacy of a combination of agents, means any measured effect of the combination which is similar to the effect predicted from a sum of the effects of the individual agents.

Chemotherapeutic Drugs

For any of the claims, a chemotherapeutic drug may be any one or more drug(2) used for chemotherapy. The drugs may be in any form such as, for example, in liposomal form enclosed inside a liposome, slow release form or in depot forms. Examples of such drugs include ABVD;
AC;
ACE;
Abiraterone (Zytiga);
Abraxane;
Abstral;
Actinomycin D;
Actiq;
Adriamycin;
Afatinib (Giotrif);
Afinitor;
Aflibercept (Zaltrap);
Aldara;
Aldesleukin (IL-2, Proleukin or interleukin 2);
Alemtuzumab (MabCampath);
Alkeran;
Amsacrine (Amsidine, m-AMSA);
Amsidine;
Anastrozole (Arimidex);
Ara C;
Aredia;
Arimidex;
Aromasin;
Arsenic trioxide (Trisenox, ATO);
Asparaginase (Crisantaspase, Erwinase);
Axitinib (Inlyta);
Azacitidine (Vidaza);
BEACOPP;
BEAM;
Bendamustine (Levact);
Bevacizumab (Avastin);
Bexarotene (Targretin);
Bicalutamide (Casodex);
Bleomycin;
Bleomycin, etoposide and platinum (BEP);
Bortezomib (Velcade);
Bosulif;
Bosutinib (Bosulif);
Brentuximab (Adcetris);
Brufen;
Buserelin (Suprefact);
Busilvex;
Busulfan (Myleran, Busilvex);
CAPE-OX;
CAPOX;
CAV;
CAVE;
CCNU;
CHOP;
CMF;
CMV;
CVP;
Cabazitaxel (Jevtana);
Cabozantinib (Cometriq);
Caelyx;
Calpol;
Campto;
Capecitabine (Xeloda);
Caprelsa;
Carbo MV;
CarboTaxol;
Carboplatin;
Carboplatin and etoposide;
Carboplatin and paclitaxel;
Carmustine (BCNU, Gliadel);
Casodex;
Ceritinib (Zykadia);
Cerubidin;
Cetuximab (Erbitux);
ChIVPP;
Chlorambucil (Leukeran);
Cisplatin;
Cisplatin and Teysuno;
Cisplatin and capecitabine (CX);
Cisplatin, etoposide and ifosfamide (PEI);
Cisplatin, fluorouracil (5-FU) and trastuzumab;
Cladribine (Leustat, LITAK);
Clasteon;
Clofarabine (Evoltra);
Co-codamol (Kapake, Solpadol, Tylex);
Cometriq;
Cosmegen;
Crisantaspase;
Crizotinib (Xalkori);
Cyclophosphamide;
Cyclophosphamide, thalidomide and dexamethasone (CTD);
Cyprostat;
Cyproterone acetate (Cyprostat);
Cytarabine (Ara C, cytosine arabinoside);
Cytarabine into spinal fluid;
Cytosine arabinoside;
DHAP;
DTIC;
Dabrafenib (Tafinlar);
Dacarbazine (DTIC);
Dacogen;
Dactinomycin (actinomycin D, Cosmegen);
Dasatinib (Sprycel);
Daunorubicin;
De Gramont;
Decapeptyl SR;
Decitabine (Dacogen);
Degarelix (Firmagon);
Denosumab (Prolia, Xgeva);
Depocyte;
Dexamethasone;
Diamorphine;
Disodium pamidronate;
Disprol;
Docetaxel (Taxotere);
Docetaxel, cisplatin and fluorouracil (TPF);
Doxifos;
Doxil;
Doxorubicin (Adriamycin);
Doxorubicin and ifosfamide (Doxifos);
Drogenil;
Durogesic;
EC;
ECF;
EOF;
EOX;
EP (Etoposide and cisplatin);
ESHAP;
Effentora;
Efudix;
Eldisine;
Eloxatin;

Enzalutamide;
Epirubicin (Pharmorubicin);
Epirubicin cisplatin and capecitabine (ECX);
Epirubicin, carboplatin and capecitabine (ECarboX);
Eposin;
Erbitux;
Eribulin (Halaven);
Erlotinib (Tarceva);
Erwinase;
Estracyt;
Etopophos;
Etoposide (Eposin, Etopophos, Vepesid);
Everolimus (Afinitor);
Evoltra;
Exemestane (Aromasin);
FAD;
FEC;
FEC-T chemotherapy;
FMD;
FOLFIRINOX;
FOLFOX;
Faslodex;
Femara;
Fentanyl;
Firmagon;
Fludara;
Fludarabine (Fludara);
Fludarabine, cyclophosphamide and rituximab (FCR);
Fluorouracil (5FU);
Flutamide;
Folinic acid, fluorouracil and irinotecan (FOLFIRI);
Fulvestrant (faslodex);
G-CSF;
Gefitinib (Iressa);
GemCarbo (gemcitabine and carboplatin);
GemTaxol;
Gemcitabine (Gemzar);
Gemcitabine and capecitabine (GemCap);
Gemcitabine and cisplatin (GC);
Gemcitabine and paclitaxel (GemTaxol);
Gemzar;
Giotrif;
Gliadel;
Glivec;
Gonapeptyl Depot;
Goserelin (Zoladex);
Goserelin (Zoladex, Novgos);
Granulocyte colony stimulating factor (G-CSF);
Halaven;
Herceptin;
Hycamtin;
Hydrea;
Hydroxycarbamide (Hydrea);
Hydroxyurea;
I-DEX;
ICE;
IL-2;
IPE;
Ibandronic acid;
Ibritumomab (Zevalin);
Ibrutinib (Imbruvica);
Ibuprofen (Brufen, Nurofen);
Iclusig;
Idarubicin (Zavedos);
Idarubicin and dexamethasone;
Idelalisib (Zydelig);
Ifosfamide (Mitoxana);
Imatinib (Glivec);
Imiquimod cream (Aldara);
Imnovid;
Instanyl;
Interferon (Intron A);
Interleukin;
Intron A;
Ipilimumab (Yervoy);
Iressa;
Irinotecan (Campto);
Irinotecan and capecitabine (Xeliri);
Irinotecan de Gramont;
Irinotecan modified de Gramont;
Javlor;
Jevtana;
Kadcyla;
Kapake;
Keytruda;
Lanreotide (Somatuline);
Lanvis;
Lapatinib (Tyverb);
Lenalidomide (Revlimid);
Letrozole (Femara);
Leukeran;
Leuprorelin (Prostap, Lutrate);
Leustat;
Levact;
Liposomal doxorubicin;
Litak;
Lomustine (CCNU);
Lynparza;
Lysodren;
MIC;
MMM;
MPT;
MST Continus;
MVAC;
MVP;
MabCampath;
Mabthera;
Maxtrex;
Medroxyprogesterone acetate (Provera);
Megace;
Megestrol acetate (Megace);
Melphalan (Alkeran);
Mepact;
Mercaptopurine (Xaluprine);
Methotrexate;
Methyl prednisolone;
Mifamurtide (Mepact);
Mitomycin C;
Mitotane;
Mitoxana;
Mitoxantrone (Mitozantrone);
Morphgesic SR;
Morphine;
Myleran;
Myocet;
Nab-paclitaxel;
Nab-paclitaxel (Abraxane);
Navelbine;
Nelarabine (Atriance);
Nexavar;
Nilotinib (Tasigna);
Nintedanib (Vargatef);
Nipent;
Nivolumab (Opdivo);

Novgos;
Nurofen;
Obinutuzumab (Gazyvaro);
Octreotide;
Ofatumumab (Arzerra);
Olaparib (Lynparza);
Oncovin;
Onkotrone;
Opdivo;
Oramorph;
Oxaliplatin (Eloxatin);
Oxaliplatin and capecitabine (Xelox);
PAD;
PC (paclitaxel and carboplatin, CarboTaxol);
PE;
PMitCEBO;
POMB/ACE;
Paclitaxel (Taxol);
Paclitaxel and carboplatin;
Pamidronate;
Panadol;
Panitumumab (Vectibix);
Paracetamol;
Pazopanib (Votrient);
Pembrolizumab (Keytruda);
Pemetrexed (Alimta);
Pemetrexed and carboplatin;
Pemetrexed and cisplatin;
Pentostatin (Nipent);
Perjeta;
Pertuzumab (Perjeta);
Pixantrone (Pixuvri);
Pixuvri;
Pomalidomide (Imnovid);
Ponatinib;
Potactasol;
Prednisolone;
Procarbazine;
Procarbazine, lomustine and vincristine (PCV);
Proleukin;
Prolia;
Prostap;
Provera;
Purinethol;
R-CHOP;
R-CVP;
R-DHAP;
R-ESHAP;
R-GCVP;
RICE;
Raloxifene;
Raltitrexed (Tomudex);
Regorafenib (Stivarga);
Revlimid;
Rituximab (Mabthera);
Sevredol;
Sodium clodronate (Bonefos, Clasteon, Loron);
Solpadol;
Sorafenib (Nexavar);
Steroids (dexamethasone, prednisolone, methylprednisolone);
Streptozocin (Zanosar);
Sunitinib (Sutent);
Sutent;
TAC;
TIP;
Tafinlar;
Tamoxifen;
Tarceva;
Targretin;
Tasigna;
Taxol;
Taxotere;
Taxotere and cyclophosphamide (TC);
Temodal;
Temozolomide (Temodal);
Temsirolimus;
Tepadina;
Teysuno;
Thalidomide;
Thiotepa (Tepadina);
Tioguanine (thioguanine, 6-TG, 6-tioguanine);
Tomudex;
Topotecan (Hycamtin, Potactasol);
Torisel;
Trabectedin (Yondelis);
Trastuzumab (Herceptin);
Trastuzumab emtansine (Kadcyla);
Treosulfan;
Tretinoin (Vesanoid, ATRA);
Triptorelin;
Trisenox;
Tylex;
Tyverb;
VIDE;
Vandetanib (Caprelsa);
Vargatef;
VeIP;
Vectibix;
Velbe;
Velcade;
Vemurafenib (Zelboraf);
Vepesid;
Vesanoid;
Vidaza;
Vinblastine (Velbe);
Vincristine;
Vincristine, actinomycin D (dactinomycin) and cyclophosphamide (VAC);
Vincristine, actinomycin and ifosfamide (VAI);
Vincristine, doxorubicin and dexamethasone (VAD);
Vindesine (Eldisine);
Vinflunine (Javlor);
Vinorelbine (Navelbine);
Vismodegib (Erivedge);
Votrient;
XELOX;
Xalkori;
Xeloda;
Xgeva;
Xtandi;
Yervoy;
Yondelis;
Z-DEX;
Zaltrap;
Zanosar;
Zavedos;
Zelboraf;
Zevalin;
Zoladex (e.g. breast cancer);
Zoladex (e.g. prostate cancer);
Zoledronic acid (Zometa);
Zometa;
Zomorph;

Zydelig; and
Zytiga.

Additional Definitions 2-5A 2',5' oligoadenylates;
ACTG AIDS Clinical Trial Group;
ADL Activities of Daily Living;
AE Adverse Events;
AIDS Acquired Immune Deficiency Syndrome;
ALT Alanine Amino Transferase (liver enzyme);
AMP AMPLIGEN Study;
AST Aspartate Amino Transferase (liver enzyme);
ATC Anatomical Therapeutic Chemical;
AUC Area under the curve;
B-cells—are also Humoral Cells;
BIW Twice a Week;
BUN Blood Urea Nitrogen;
C Cytidine;
CBC Complete Blood Test;
CCL22 C-C Motif Chemokine Ligand 22;
CD Cognitive Deficit Subscale;
CD-1 Cluster of Differentiation 1;
CD4 Cluster of Differentiation 4;
CD40 Costimulatory Protein 40;
CD8+ Cluster of Differentiation 8, Transmembrane Glycoprotein;
CD80 Costimulatory Protein 80;
CD86 Costimulatory Protein 86;
CDC Center for Disease Control;
CFS Chronic Fatigue Syndrome;
Cmax Maximum Concentration of Drug in the Blood;
CMV Cytomegalovirus;
CR Complete Response;
CTL Cytotoxic T Lymphocytes;
CT Scan Computed Tomography Scan;
CXCL10 C-X-C Motif Chemokine 10;
DC Dendritic Cells;
DIS Diagnostic Interview Schedule;
DNA Deoxyribonucleic Acid;
dsDNA Double Stranded DNA;
dsRNA Double Stranded RNA;
DTH Delayed-Type Hypersensitivity;
EAP Early Access Program;
EEA European Economic Area;
eIF2 Eukaryotic Initiation Factor 2;
ETT Exercise Tolerance Testing;
EU European Union;
FDA Food and Drug Administration;
GHP General Health Perception (Index);
GI Gastro Intestinal;
I Inosine;
IACUC Institutional Animal Care and Use Committee;
ICD-10;
International Statistical Classification of Diseases and Related Health Problems, Revision 10;
IFN Interferon;
IFN-α Interferon-Alpha;
IFN-γ Interferon Gamma;
IFN-I Interferon Type I;
IFN-ß Interferon Beta;
IL-1 A group of 11 cytokines, which plays a central role in the regulation of immune and inflammatory responses to infections or sterile insults;
IL10 Interleukin 10, also known as human cytokine synthesis inhibitory factor (CSIF), is an anti-inflammatory cytokine;
IL-12 Interleukin that is naturally produced by dendritic cells, macrophages and human B-lymphoblastoid cells in response to antigenic stimulation;
IL-12p70 Key Cytokine for the Induction of Th1 Immune Responses;
INN International Non-proprietary Name;
IRF3 Interferon Regulatory Transcription Factor 3;
IRF7 Interferon Regulatory Transcription Factor 7;
ITT Intent-to-Treat;
IV Intravenous;
K80-K87 ICD-10 Code for Disorders of Gallbladder, Biliary Tract and Pancreas;
KPS Karnofsky Performance Status;
LAK Lymphokine-activated Killer;
LDH Lactic Acid Dehydrogenase (liver enzyme);
LPS Lipopolysaccharide;
IL6 Interleukin 6—an interleukin that acts as both a pro-inflammatory cytokine and an anti-inflammatory myokine;
mAb Monoclonal Antibody;
min Minutes;
mRNA Messenger RNA;
MTD Maximum Tolerated Dose;
NDA New Drug Application;
NF-kB Nuclear Factor Kappa-light-chain-enhancer of Activated B Cells;
NHP Non-Human Primates;
NLR Neutrophil to Lymphocyte Ratio;
NK Natural Killer Cells;
non-IFNα or non-IFNalpha Non Interferon Alpha;
OS Overall Survival;
p68 Novel transcriptional coactivator of the p53 tumour suppressor;
PAMP Pathogen Associated Molecular Pattern;
PB Peripheral Blood;
PBMC Peripheral Blood Mononuclear Cells;
PD-1 Programmed Cell Death-1;
PD-L-1 Programmed Death-Ligand 1;
PK Pharmacokinetics;
PK/PD Pharmacokinetic and Pharmacodynamic Studies;
PKR Protein Kinase R;
PR Partial Response;
PT Prothrombin Time;
PTT Partial Thromboplastin Time;
QT Interval Represents electrical depolarization and repolarization of the ventricles;
RBC Red Blood Cells;
RCC Renal Cell Carcinoma;
RECIST Response Evaluation Criteria In Solid Tumors;
rIFNα-2b or rIFNalpha-2b Recombinant Interferon Alpha 2b;
RNA Ribonucleic Acid;
RNAse Enzyme that catalyzes the degradation of RNA into smaller components;
SAE Serious Adverse Events;
SARS Severe Acute Respiratory Syndrome;
SCL-90-R Symptom Checklist 90 Revised;
SGOT Serum Glutamic Oxaloacetic Transaminase;
SII Systemic Immune-Inflammation Index;
SOC Standard of Care;
ssRNA Single Stranded RNA;
T½ Biological Half-Life;
T3 Triiodothyronine;
T4 Thyroxine;
T-cells Lymphocyte of a type produced or processed by the thymus gland;
TCR T Cell Receptor;

Teff T Effector Cells;
TIL Tumor Infiltrating Lymphocytes;
TME Tumor Microenvironment;
TLR Toll-Like Receptor;
TLR3 Toll-Like Receptor 3;
TNF-α Tumor Necrosis Factor Alpha;
Treg Regulatory T Cells;
TSH Thyroid-stimulating Hormone;
U Uridine;
USAN United States Adopted Names;
WBC White Blood Cells;
WEEV Western Equine Encephalitis Virus; and
WHO World Health Organization.

As used herein, the terms "patient" or "subject" are used interchangeably and mean a mammal, including, but not limited to, a human or non-human mammal, such as a bovine, equine, canine, ovine, or feline. Preferably, the patient is a human.

As used herein, "survival" refers to the patient remaining alive, and includes overall survival as well as progression free survival. 1-year survival rate and 2-year survival rate refers to the K-M estimate of the proportion of subjects alive at 12 month or 24 months.

By "extending survival" is meant increasing overall survival and/or progression free survival in a treated patient relative to a control treatment protocol, such as treatment with only ipilimumab. Survival is monitored for at least about one month, two months, four months, six months, nine months, or at least about 1 year, or at least about 2 years, or at least about 3 years, or at least about 4 years, or at least about 5 years, or at least about 10 years, etc., following the initiation of treatment or following the initial diagnosis.

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated, the presence or size of metastases, or the size of the primary tumor.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc. In some aspects of this and other embodiments, the subject is a mammal. Preferably, the mammal is selected from the group consisting of humans, primates, farm animals, and domestic animals. More preferably, the mammal is a human.

In the present invention, an "effective amount" or a "therapeutically effective amount" of an agent, monoclonal antibody, or fragment thereof or a compound or composition disclosed herein is an amount of such material that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of any active agent disclosed herein or a composition containing the same will be that amount of the active agent or composition, which is the lowest dose effective to produce the desired effect.

As used herein, "tumors" and "cancers" are used interchangeably. Tumors may be benign or malignant. As used herein, the "stromal microenvironment" includes those stromal cells that are in a tumor cell's microenvironment and support the growth of tumor cells.

In this embodiment, "contacting" means bringing, e.g., a immune checkpoint inhibitor, and/or one or more additional therapeutic agents into close proximity to the tumor microenvironment. This may be accomplished using conventional techniques of drug delivery to mammals or in the in vitro situation by one or more additional therapeutic agents to a culture media in which the cancer cells are located.

EXAMPLES

Example 1: Experimental Results

Currently surgery is the only potentially curative option for pancreatic cancer, but only around 15% of patients are eligible at initial diagnosis since most pancreatic cancers are detected in an advanced stage of the disease. Around 20% of patients are diagnosed with locally advanced pancreatic cancer and the remaining 65% present with metastatic disease.

The current standard of care (SOC) for locally advanced and metastatic pancreatic carcinoma is FOLFIRINOX, a four drug cocktail with significant toxicity. Approval of FOLFIRJNOX was based on the Phase 2/3 ACCORD study published in 2011 (Von Hoff et al., 2011). In this study, FOLFIRINOX was compared to Gemcitabine, which was the SOC at that time.

The result of the ACCORD study is that overall survival (OS) increased from 6.8 months with Gemcitabine to 11.1 months with FOLFIRINOX ($p<0.001$). However, the Complete Response Rate (CR) was only 0.6%. Moreover, overall mean survival with second line therapy following progression on the FOLFIRINOX was only 4.05 months. It is clear that new treatment options are desperately needed for this devastating malignancy.

One of these novel therapeutic options is immunotherapy which has shown to be a promising treatment strategy. Essential in this therapeutic strategy is to boost the patient's immune system, by reversing the tumor-antigen specific T-cell tolerance induced by their tumor.

One goal in immunotherapy is reprogram of the tumor microenvironment (TME) to convert "cold" tumors into "hot" tumors that will be responsive to checkpoint blockade. The goal is to unleash the cellular immune response to attack and destroy cancer cells and increase survival by increasing intratumoral Teff cells while decreasing intratumoral Treg cells.

Surprisingly, AMPLIGEN is capable to promote selective attraction of CTLs (Teff) with concomitant reduction in Treg attraction in the TME based on our observations.

An ability to increase Teff (CD8+ T cells) and reducing Treg cells in the TME has significant advantages. In Pancreatic Cancer tumor infiltrating CD4+ T (high)/CD8+ T (high)/Treg (low) in the TME are independent prognosticators of increased overall survival.

In pancreatic cancer, Treg infiltration into the TME is a bad prognostic indicator for survival. Hiraoka et al. divided pancreatic cancer patients into two cohorts based on values of the Treg cells being higher or lower than the median value in the TME, the low Treg group showed significantly better survival than the high Treg group (Hiraoka, et al., 2006).

Our discovery that AMPLIGEN can increase the Teff cell to Treg cell ratio thereby converting a "cold" pancreatic TME into a "hot" pancreatic TME is highly relevant for improving the likelihood of an antitumor response to checkpoint blockade.

Data in a preclinical model of pancreatic cancer, the combination of AMPLIGEN and checkpoint blockade (anti-PD-L1) is found to be synergistic for increasing both overall survival and time-to-tumor progression.

We propose the use of AMPLIGEN in combination with checkpoint blockade to improve the ability to treat cancer. Or more specifically, so that AMPLIGEN and the checkpoint blockade can perform synergistically. That is, we expect that the (effect of AMPLIGEN+checkpoint blockade) is greater than that of the (effect of AMPLIGEN)+(effect of checkpoint blockade).

We have also found that an animal model in melanoma combining AMPLIGEN with an anti-PD-L1 showed a threefold increase in overall tumor response rate (RECIST Criteria). In addition, in a transgenic mouse model, combining AMPLIGEN with an anti-PD-L1 drug in pancreatic cancer, shows a synergistic increase in median survival. Moreover, we found in a mouse model of colorectal carcinoma that the AMPLIGEN+anti-PD-L1 combination showed a median survival increase of greater than 2.5 fold, compared to anti-PD-L1 alone.

Basis for Barriers to Immunotherapy in Pancreatic Carcinoma

The TME in pancreatic cancer is dominated by immunosuppressive cells including Treg cells and lacks Teff cells needed to drive an anti-tumor response. In a minority of patients with lower prevalence of Treg cells in the TME, a better prognosis was seen.

Importantly, the lack of T effector cells in the TME of patients with pancreatic carcinoma appears to be related to the failure of these T effector cells to migrate from the bone marrow and blood of pancreatic cancer patients to the TME, since high levels of tumor-reactive T cells were easily found in bone marrow samples of patients with pancreatic carcinoma. Thus, these findings suggest that the failure of immunotherapy in pancreatic carcinoma is not because of a lack of antigenicity of the tumor itself or a lack of T effector cells directed against tumor antigens, but a failure to recruit T effector cells into the TME while at the same time reducing the level of Treg cells in the TME.

Increasing the Ratio of Teffector/Treg Cells in the TME Using AMPLIGEN (Rintatolimod)

Colorectal carcinoma was used as a GI model for pancreatic carcinoma in order to obtain biopsy specimens of the TME. We used AMPLIGEN to determine if there is improvement in the Teff/Treg ratio in the TME secondary to the AMPLIGEN induction of desirable chemokines, such as CXCL 10 (Teff-attractant), in the TME, while decreasing the unfavorable chemokines, such as CCL22 (Treg-attractant), thereby increasing the Teff/Treg ratio in the TME.

We have seen that AMPLIGEN improves the TME in another gastrointestinal cancer, colorectal carcinoma. A colorectal carcinoma trial of AMPLIGEN plus rIFNa-2b and celecoxib produced an increased ratio of CXCL 10 to CCL22 in the TME along with an increase in the ratio of Teff/Treg markers in nine patients with metastatic colorectal carcinoma compared to controls. See, Example Section below.

Based on our experiments, we found that AMPLIGEN (rintatolimod) shows an ability to convert "cold" tumors into "hot" tumors which is much more likely to respond to checkpoint blockage.

We propose that in Pancreatic Cancer tumor infiltrating CD4+T (high)/CD8+T (high)/% Treg (low) in the TME are independent prognosticators of increased overall survival. In Pancreatic Cancer Treg infiltration into the TME is a bad prognostic indicator for survival. Pancreatic cancer patients were divided into two cohorts based on values of the Treg cells being higher or lower than the median value in the TME, the low Treg group showed significantly better survival than the high Treg group.

Results: Sill data available up to 18 weeks on 9 patients with metastatic disease receiving AMPLIGEN IV 400 mg twice weekly. A decrease in SIII is a favorable prognostic sign for increased survival.

The potential of AMPLIGEN to increase the Teff cell to Treg cell ratio thereby converting a "cold" pancreatic TME into a "hot" pancreatic TME is highly relevant for improving the likelihood of an antitumor response to checkpoint blockade. A combination of AMPLIGEN and checkpoint blockade (anti-PD-LI) was synergistic in increasing both overall survival and time-to-tumor progression.

Summary of data showing AMPLIGEN Plus Checkpoint Blockage (Checkpoint Inhibitor) Synergistically Increased Survival In a pancreatic cancer transgenic mouse model, combining AMPLIGEN with an anti-PD-LI drug shows a synergistic increase in median survival.

In a mouse model of colorectal carcinoma, the combination of AMPLIGEN plus anti-PD-I showed a median survival increase of greater than 250% compared to anti-PD-I alone.

Pre-clinical cancer studies using mouse models of three different solid tumors show synergistic antitumor activity and/or increased median survival when AMPLIGEN was combined with checkpoint blockade, compared to checkpoint blockade alone.

Animal model in melanoma combining AMPLIGEN with an anti-PD-L1 showed a threefold increase in overall response rate (RECIST Criteria). In addition, a study using a transgenic mouse model combining AMPLIGEN with an anti-PD-LI drug in pancreatic cancer shows a synergistic increase in median survival. Moreover, in a mouse model of colorectal carcinoma, the AMPLIGEN combination showed a median survival increase of greater than 2.5 fold, compared to anti-PD I alone.

AMPLIGEN Induced Anti-tumor Synergy in a Melanoma Model with Checkpoint Immune Suppression Blockade.

AMPLIGEN was synergistic with anti-PD-LI, yielding an increased anti-tumor response in a B 16 mouse melanoma model. The decrease in tumor size was significant for the AMPLIGEN 250 µg+anti-PD-LI cohort compared to anti-PD-LI cohort alone (p=0.023)

Addition of AMPLIGEN to anti-PD-LI increased the objective response rate 300%, from 10% with anti-PD-LI alone to 30% with the combination.

Example 2: Pancreatic Cancer

According to the Pancreatic Cancer Action Network, Pancreatic cancer is the fourth leading cause of cancer death in the U.S. It is the only cancer of the most commonly diagnosed with a five-year survival rate at just six percent. Pancreatic cancer is anticipated to move from the fourth to the second leading cause of cancer death in the U.S. by 2020, based on current projections. Accordingly, both the projected number of new pancreatic cancer cases and pancreatic cancer deaths will more than double by 2030 (Matrisian et al., 2012).

Figure 2:
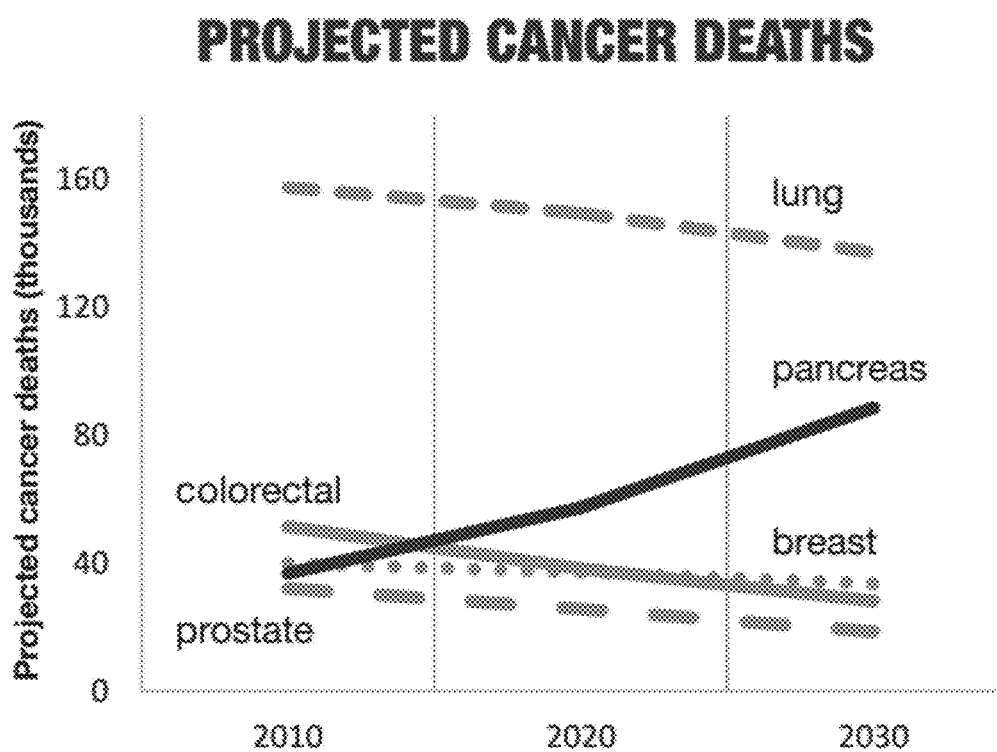
FIG. 2 depicts projected cancer deaths for the major cancer killers in the US.

FIG. 2 depicts projected cancer deaths for the major cancer killers in the US.

In the EU, incidence is continuing to increase and death rate is projected to increase by ~30% to ~112,000 new cases per year by 2025.

Figure 3:
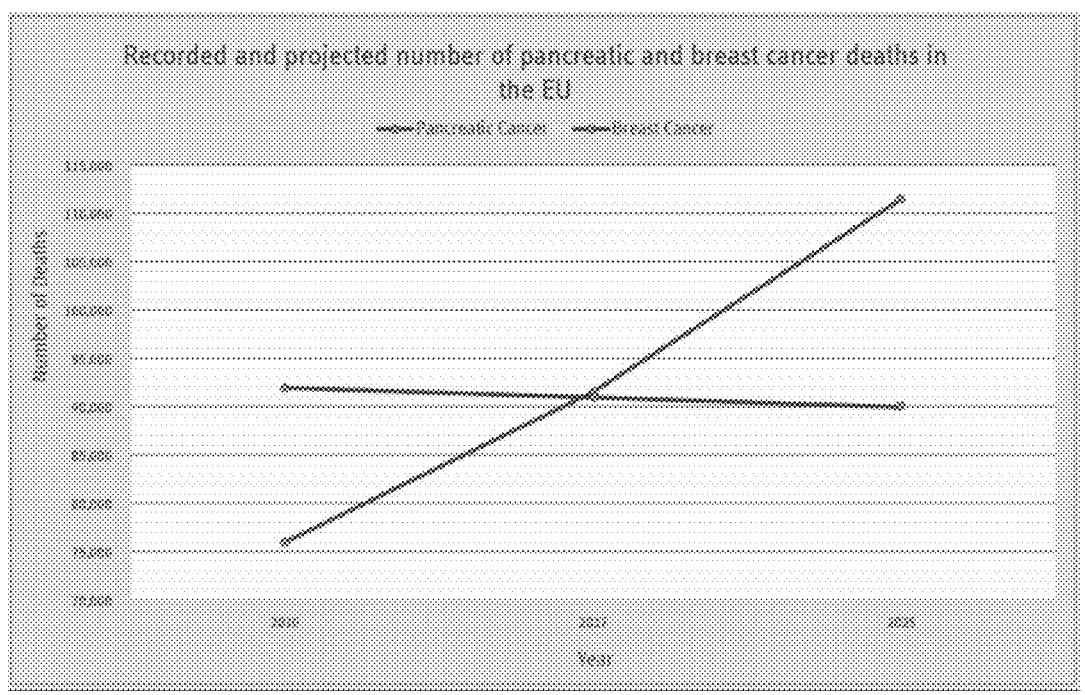
FIG. 3 depicts projected pancreatic and breast cancer deaths in the EU by 2025.

FIG. 3: Projected Pancreatic and Breast Cancer Deaths in the EU by 2025

Pancreatic cancer is associated with an overall five-year survival of 5% and thus contributes significantly to cancer-related mortality. A recent paper predicted that pancreatic cancer will be the second leading cause of cancer-related deaths before 2030. Currently surgery is the only potentially curative option, but only around 15% of patients are eligible at initial diagnosis since most pancreatic cancers are detected in an advanced stage of the disease. Around 20% of patients are diagnosed with locally advanced pancreatic cancer and the remaining 30-50% present with metastatic disease. It is clear that new treatment options are desperately needed for this devastating malignancy.

The pancreas gland itself is located in the abdomen between the stomach and the spine. It is approximately 6 inches long, and shaped like a pear lying on its side. It is categorized into three sections; the head, or the wider part of the pancreas; the body, or the middle section; and the tail, the narrow end of the pancreas. https://world wide web.cancer-.gov/types/pancreatic/patient/pancreatic-treatment-pdq Pancreatic cancer, or carcinoma of the pancreas, is a disease in which malignant (cancer) cells form in the tissue of the pancreas. The pancreas is a gland that aids in digestion. It makes juices that break down food with exocrine pancreas cells. It also produces hormones, such as insulin and glucagon to help control blood sugar with endocrine pancreas cells. Most pancreatic cancers start in the exocrine cells. Due to the absence of symptoms in the early stages of pancreatic cancer, the majority of patients are diagnosed when the cancer has spread locally or to other parts of the body.

Pancreatic cancer is a very severe and life-threatening disease that is associated with shortened life expectancy.

Etiologic factors that are linked to the development of adenocarcinoma of the pancreas in adulthood include both tobacco smoking and environmental exposure to tobacco smoking, especially during childhood or in utero from maternal smoking. Smoke from tobacco is estimated to contribute to the development of 20-30% of pancreatic cancer.

Several infectious diseases including *Helicobacter pylori* and hepatitis B also have a positive association with pancreatic adenocarcinoma. Occupational factors have also been linked to 12-29% of cases and include exposure to a wide range of chemicals/solvents such as chlorinated hydrocarbons, polycyclic aromatic hydrocarbons, insecticides, and aliphatic solvents.

Demographic risk factors for pancreatic adenocarcinoma include age between 60-80, African American race, low socioeconomic status, and Ashkenazic Jewish heritage. Several medical conditions with increased risk of pancreatic cancer include diabetes mellitus, chronic cirrhosis, pancreatitis, and a prior cholecystectomy.

Finally, genetic predisposition also plays a minor role in pancreatic cancer risk with 10-20% of pancreatic cancer having a familial link.

TABLE 1

Etiologic Risk Factors for Development of Pancreatic Cancer

| Etiologic Factor | % Contribution* |
|---|---|
| 1) Tobacco Smoke | 20-30% |
| 2) Infectious Disease | — |
| 3) Occupational | 12-29% |
| 4) Demographics | — |
| 5) Medical Conditions | — |
| 6) Genetic | 20-20% |

*% Contribution shown if available

Specific Characteristics; Pathophysiological, Histopathological, Clinical Characteristics In recent years evidence has accumulated that tumor infiltrating lymphocytes (TILs) have a major effect on several important clinical attributes of cancer. It has been shown that type, density and location of T cells in tumors provide a better prognostic value that was superior to, and independent of those of the TNM classification criteria. In pancreatic cancer the CD8+T lymphocytes present the predominant T lymphocyte subset, and are associated with favorable clinical outcome. However, it is generally accepted that aside from CD8 T cell number in the tumor environment, more specific analysis of the T cells (Teff vs Treg) result in better prognostic or predictive markers in pancreatic cancer (treatment). Thus, analyses of the TME, in particular with respect to the characterization of both the Teff and Treg cells reveals important immune signatures in pancreatic tumors.

Aside from these local immune markers, also in peripheral blood (PB) prognostic and predictive markers have been found. The neutrophil to lymphocyte ratio (NLR) in peripheral blood has shown to be a prognostic marker in pancreatic cancer (Kawahara et al., 2016). The use of (bio)markers from PB is advantageous over local tumor tissue since this is less invasive for patients and can be measured longitudinally over the course of treatment. Currently, the enumeration, activation, presence of regulatory T cells, and co-signaling signature of TILs and PB T cells in pancreatic tumor patients is under investigation. At least in some cases, PB T cells may reflect the TIL co-signaling signature, and thus could serve as a surrogate marker for local immune status at diagnosis and during therapy. Tumor cell free DNA (cfDNA) found in peripheral blood is being actively investigated and is believed will become widely used in the future as a surrogate (liquid biopsy) for direct tumor biopsies with the advantage of metatastatic disease sampling.

Pancreatic cancer is difficult to detect and diagnose for the following reasons: (1) There are no noticeable signs or symptoms in the early stages of pancreatic cancer. (2) The signs of pancreatic cancer, when present, are like the signs of many other illnesses, such as pancreatitis or an ulcer. (3) The pancreas is obscured by other organs in the abdomen and is difficult to visualize clearly on imaging tests.

To appropriately treat pancreatic cancer method, it is preferred to evaluate whether the cancer can be resected. Diagnostic tools used include Imaging, Peritoneal Cytology, and Tumor Markers. Imaging can be used to detect tumors, and to determine if the tumor is resectable.

Symptoms of pancreatic cancer include, for example, jaundice; light-colored stools or dark urine; pain in the upper or middle abdomen and back; weight loss for no known reason; loss of appetite; fatigue.

We hypothesizes that AMPLIGEN, being a dsRNA, will mainly activate antigen presenting cells. This in turn could lead to increased numbers of monocytes and dendritic cells which subsequently could lead to increased numbers CD8 T cells and decreased numbers of regulatory T cells or myeloid derived suppressor cells.

Conventional treatment of Pancreatic cancers are wanting. The current standard of care (SOC) for locally advanced and metastatic pancreatic carcinoma is FOLFIRINOX, a four drug cocktail with significant toxicity. Approval of FOLFIRINOX was based on the Phase 2/3 ACCORD study published in 2011 (Von Hoff et al., 2011). In this study, FOLFIRINOX was compared to Gemcitabine, which was the SOC at that time.

TABLE 3

First Line Therapy: Results of the ACORD Study*

| Parameter | FOLFIRINOX | Gemcitabine | p-value |
|---|---|---|---|
| Overall Survival (OS) months | 11.1 | 6.8 | p < 0.001 |
| Progression Free Survival (PFS) months | 6.4 | 3.3 | p < 0.001 |
| Complete Response Rates (CR) n (%) | 1 (0.6) | 0 (0) | — |
| Partial Response Rates (PR) n (%) | 53 (31.0) | 16 (9.4) | p < 0.001 |

*n = 171 FOLFIRINOX arm
n = 171 Gemcitabine arm

Conroy et al. *NEJM* 2011; 364(19):1817

Table 3 shows the results of the ACCORD study. Overall Survival (OS) increased from 6.8 months with Gemcitabine to 11.1 months with FOLFIRINOX (p<0.001). However, the Complete Response Rate (CR) was only 0.6%. Moreover, as shown in Table 4, overall mean survival with second line therapy following progression on the FOLFIRINOX was only 4.05 months.

TABLE 4

Survival with Second Line Therapy Following Progression on FOLFIRINOX

| Parameter | Gemcitabine Viaud, et al 2017 | Gemcitabine Gilabert, et al. 2017 | Gemcitabine da Rocha, et al. 2015 | Overall (mean) |
|---|---|---|---|---|
| Overall Survival (OS) (months) | 3.7 | n/a | 5.7 | 4.05* |
| Progression Free Survival (PFS) (months) | 2.1 | 2.5 | 2.0 | 2.24* |
| Complete Response Rates (CR) (%) | 0% | 0% | 0% | 0%* |
| Partial Response Rates (PR) (%) | 8.3% | 5.5% | 0% | 6.4%* |
| Number of Patients (n) | 96 | 72 | 20 | 188 |

*weighted average based on n in each study

These methods are not satisfactory as evidenced by the high mortality rate.

Unfortunately, the rapidly growing field of immunotherapy using checkpoint blockade has have not encountered success in patients with adenocarcinoma of the pancreas. Patients with pancreatic carcinoma show poor response rates to checkpoint blockage using anti-PD1, anti-PD-L1, and anti-CTLA-4 drugs.

The TME in pancreatic cancer is dominated by immunosuppressive cells including Treg cells and lacks Teff cells needed to drive an anti-tumor response (Liyanage et al., 2002; Hiraoka et al., 2006). In a minority of patients with lower prevalence of Treg cells in the TME, a better prognosis was seen. (Hiraoka et al., 2006).

Importantly, the lack of Teffector cells in the TME of patients with pancreatic carcinoma appears to be related to the failure of these Teffector cells to migrate from the bone marrow and blood of pancreatic cancer patients to the TME, since high levels of tumor-reactive T cells were easily found in bone marrow samples of patients with pancreatic carcinoma.

Thus, these findings suggest that the failure of immunotherapy in pancreatic carcinoma is not because of a lack of antigenicity of the tumor itself or a lack of Teffector cells directed against tumor antigens, but a failure to recruit Teffector cells into the TME while at the same time reducing the level of Treg cells in the TME.

We note that in Pancreatic Cancer tumor infiltrating CD4+T (high)/CD8+T (high)/% Treg (low) in the TME are independent prognosticators of increased overall survival (Ino et al., 2013). Further, in Pancreatic Cancer Treg infiltration into the TME is a bad prognostic indicator for survival. Hiraoka et al. divided pancreatic cancer patients into two cohorts based on values of the Treg cells being higher or lower than the median value in the TME, the low Treg group showed significantly better survival than the high Treg group (Hiraoka et al., 2006).

Figure 4:
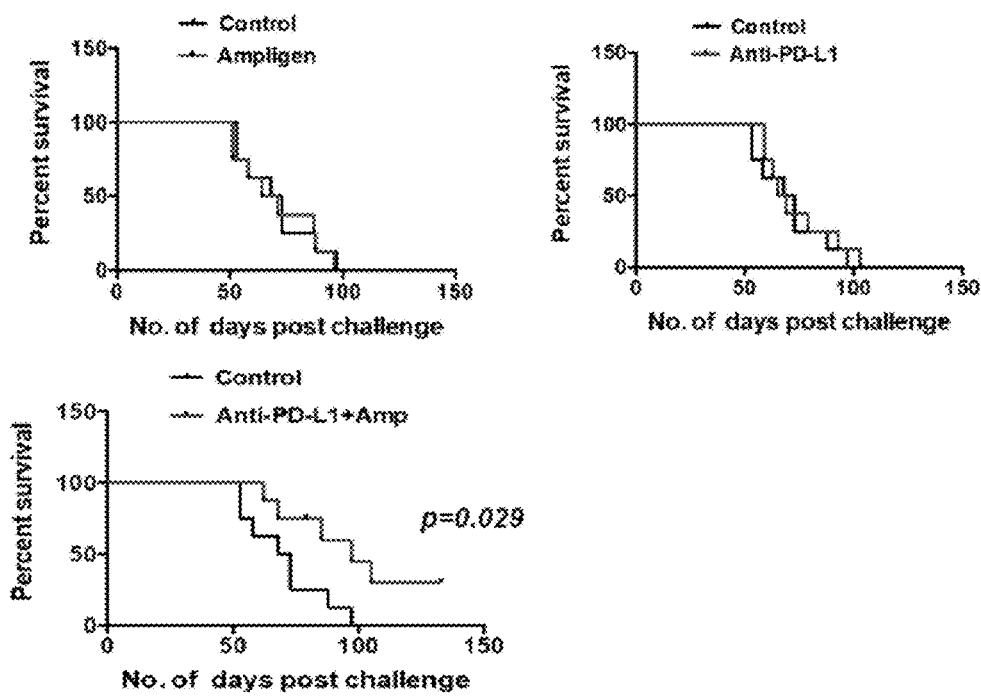
FIG. 4 depicts synergism between AMPLIGEN and checkpoint blockade.
Figure 4:
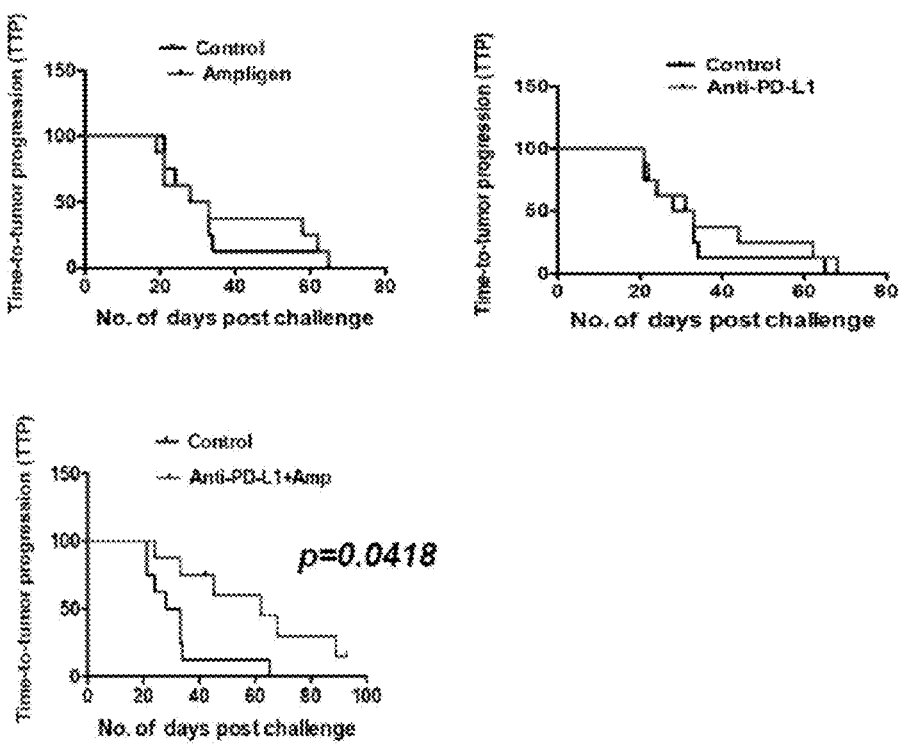

We performed experiments to determine if AMPLIGEN can increase the Teff cell to Treg cell ratio thereby converting a "cold" pancreatic TME into a "hot" pancreatic TME. This is highly relevant for improving the likelihood of an antitumor response to checkpoint blockade. As shown below in a preclinical model of pancreatic cancer, the combination of AMPLIGEN and checkpoint blockade (anti-PD-L1) was synergistic in increasing both overall survival and time-to-tumor progression (FIG. 4).

In addition, AMPLIGEN was tested in mice against pancreatic tumors in conjunction with an anti-PD-L1, and was shown to synergistically increase survival as well as time to tumor progression (p=0.029 and 0.0418, respectively).

AMPLIGEN plus Checkpoint Blockage Synergistically Increased Survival in Pancreatic. AMPLIGEN was also preliminarily tested in a pancreatic cancer transgenic mouse model, combining AMPLIGEN with an anti-PD-L1 drug shows a synergistic increase in median survival.

| Initial Results from Mouse Model of Pancreatic Cancer Using AMPLIGEN Plus Checkpoint Blockade | |
|---|---|
| Cohorts (n = 8 each) | Time to Progression Median-Days |
| 1) Control | 33 |
| 2) AMPLIGEN | 33 0* |
| 3) Anti-PD-L1 | 33 0* |
| 4) AMPLIGEN + Anti-PD-L1 | 73 40* |

*Increased Survival Over Control

Figure 5:
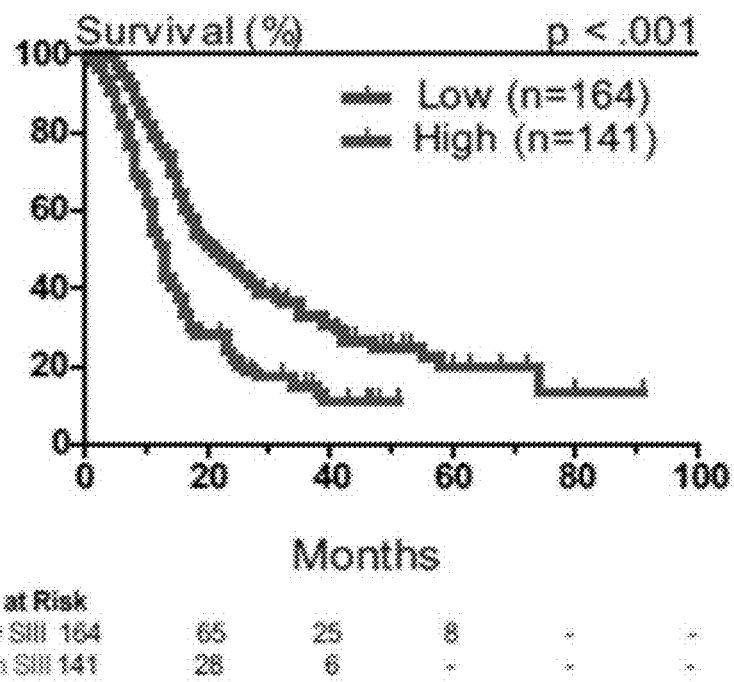
FIG. 5 depicts the survival of mice with low SIII or high SIII.

A Low Systemic Immune-Inflammation Index (SIII) Predicts Greater Survival in Pancreatic Cancer. Using the Systemic-Immune-Inflammation Index (SIII) as a Prognostic Marker in Pancreatic Cancer can predict survival in resectable pancreatic cancer. A low SIII (≤900) predicts a greater survival. SIII=Neutrophils/lymphocytes ratio (NLR)×thrombocytes. Cohorts with low SIII (N=164) compared to those with high SIII (n=141) had a significant longer survival rate (p<0.001). See, FIG. 5 where SIII=Neutrophils/lymphocytes ratio (NLR)×thrombocytes.

Figure 6:
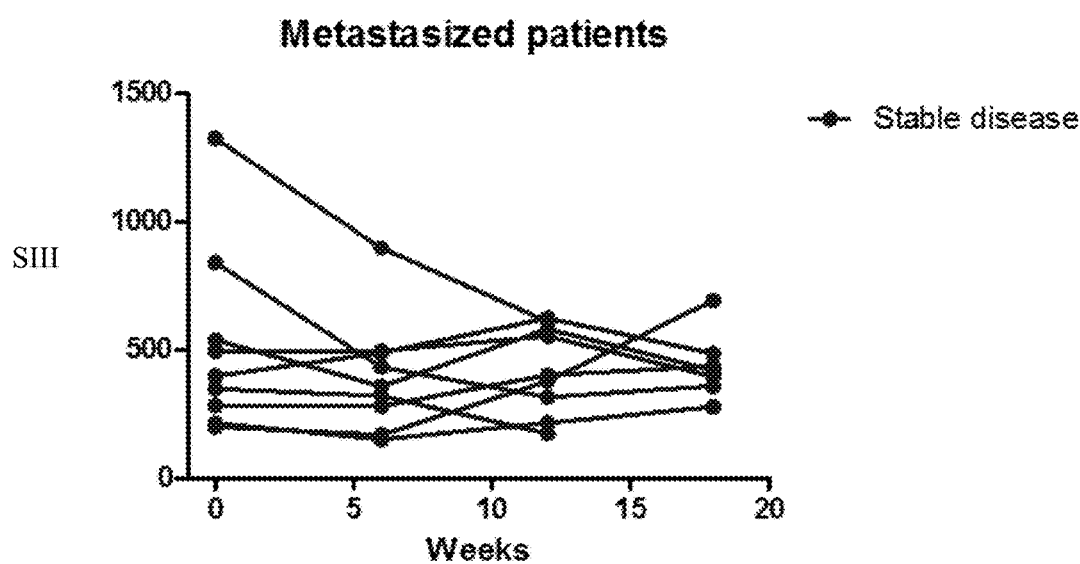
FIG. 6 depicts SIII data available up to 18 weeks on 9 patients with metastatic disease.

Early Results: SIII data available up to 18 weeks on 9 patients with metastatic disease receiving AMPLIGEN (IV) 400 mg twice weekly. See FIG. 6.

A decrease in SIII is a favourable prognostic sign for increased survival.

Preclinical Model

AMPLIGEN was tested in mice against pancreatic tumors in conjunction with an anti-PD-L1 and was shown to synergistically increase survival. See, FIG. 4, panels labeled "Percent Survival." As well as time to tumor progression. See, FIG. 4, panels labeled "Time-to-tumor progression."

Example 3: Clinical Studies in Applied Condition

Immune monitoring during rintatolimod (AMPLIGEN®) maintenance therapy in pancreatic cancer patients is performed. A single center pilot cohort study is planned. The number of initial patients may be 20 and this number may be expanded.

The entrance criteria will be 18 years and diagnosed with local or advanced metastasized cancer—in this study the cancer to study is for the cancer of the claims which is pancreatic cancer and related cancers. This is referred to as "targeted cancer" in this example only.

Entrance criteria may depend on Age, diagnosed with locally advanced or metastatic targeted cancer or completed treatment with either of the currently available standard of care treatments for the targeted cancer.

Exclusion criteria may include anemia (e.g., Hb<6.2 mmol/L) decreased renal function (e.g., <50 ml/min), elevated bilirubin levels (e.g., >1.5 times the upper limit of normal), active infection, Pregnancy, Unable to draw blood for study purposes, serious concomitant systemic disorders that would compromise the safety of the patient or his/her ability to complete the study.

Study parameters to be performed at baseline (prior to first treatment and after e.g., 6 weeks of treatment) include complete blood test (cbc) with differential and platelet count; measurement of a broad panel of immune cells as well as ligands and receptors related to t cell activation and migration; the other part of the blood samples will be used to isolate peripheral blood mononuclear cells (pbmc) and plasma which will be stored and registered for near-future analysis of t cell effector functions in vitro and usage of t cell receptor (tcr) repertoire.

Study treatment can be: cohort will receive best available Standard of Care plus AMPLIGEN® (200-400 mg) by IV infusion over 30-60 minutes, two times per week in combination with checkpoint blockade.

A drug administration log is be completed each day with signs and symptoms log including magnitude. Vital signs including temperature, blood pressure, pulse, and respiratory are taken twice daily and recorded on the vital sign log. Patient will be treated as long as they are benefiting from the treatment and/or the investigator can decide to withdraw a subject from the study for urgent medical reasons.

Evaluations is performed by determining the presence of common abnormalities in the baseline immune signature of pancreatic cancer patients who completed standard of care. Determining changes in immune signature after AMPLIGEN treatment compared to the immune signature at baseline. Further determinations may involve measuring differences in PB immune parameters as measured by FCM between baseline and after AMPLIGEN treatment will be calculated using the Mann-Whitney or the Kruskall-Wallis test, or in case of normal distributions the student t-test or one-way anova test whichever appropriate. Two-sided P-values <0.05 is considered to be significant.

Example 4: Melanoma

Similar to the pancreatic cancer success above, we also see positive results with melanomas.

The combination of rIL-2 and AMPLIGEN can potentiate host-mediated antitumor effects, yielding increased survival in a melanoma xenograft model without toxicity.

Combinatorial Immunotherapy of AMPLIGEN® (rintatolimod) Poly I: Poly C12U and Blockade of Programmed Death-Ligand 1 Against Established Melanoma Tumors in a Mouse Model Rintatolimod together with anti-PD-L1 antibodies were tested for anti-tumor activity against established subcutaneous B16 melanoma tumors in C57BL/6 mice. Mice (10 animals per group) were inoculated with 0.4×10E6 B16-F10 tumor cells in their shaved rear flanks. Seven days later (when tumors reached 0.3 to 0.5 cm in their largest diameter), mice were randomized for tumor sizes, and individually tagged and were allocated to the following six treatment groups:

No treatment (negative controls)
Rintatolimod alone 100 μg/dose 4×
Rintatolimod alone 250 μg/dose 4×
Anti-PD-L1 mAb alone
Rintatolimod 100 μg/dose 4× plus anti-PD-L1 mAb
Rintatolimod 250 μg/dose 4× plus anti-PD-L1 mAb Rintatolimod was injected intravenously at 100 or 250 micrograms/dose and was repeated 4 times, 5 days apart. Anti-PD-L1 mAb (clone 10F.9G2, BioXCell) was administered intraperitoneally on Days 1 and 3 after each rintatolimod injection at a 200 microgram/dose. Tumors were measured 3 times per week using a set of calipers, taking measurement of 2 opposing diameters and were recorded as tumor areas. Mice exhibiting ulcerated tumors or tumors larger than 2 cm diameter (any direction) were euthanized following IACUC policies.

Results were presented as tumor sizes for individual mice throughout time of therapy, average tumor size in each group and survival up to Day 30 (time to euthanasia).

Results:

Tumor Responses at Day 30

One complete tumor regression was seen by Day 30 in each of the three (3) cohorts that received the anti-PD-L1 mAb. The only cohort that had more than one significant tumor regression was the rintatolimod 250 μg+anti-PD-L1 group. As shown in Table 5 the rintatolimod 250 μg+anti-PD-L1 group had two mice with partial responses (PRs) of 70 and 86% reductions in the tumor size (per RECIST v1.1 criteria) in addition to the complete response (CR).

Summary of Tumor Responses:

AMPLIGEN was synergistic with anti-PD-L1, yielding an increased anti-tumor response in a B16 mouse melanoma model The decrease in tumor size was significant for the AMPLIGEN 250 μg+anti-PD-L1 cohort compared to anti-PD-L1 cohort alone (p=0.023).

Addition of AMPLIGEN to anti-PD-L1 increased the objective response rate 3-fold, from 10% with anti-PD-L1 alone to 30% with the combination.

TABLE 5

Tumor Responses*

| Group (n = 10) | Number of Complete Responses (CR) | Number of Partial Responses (PR) | % Tumor Reduction in PRs | Total # Tumor Responses CR + PR |
|---|---|---|---|---|
| No Treatment Control | 0 | 0 | — | 0 |
| 100 µg rintatolimod | 0 | 0 | — | 0 |
| 250 µg rintatolimod | 0 | 0 | — | 0 |
| Anti-PD-L1 | 1 | 0 | — | 1 |
| 100 µg rintatolimod + Anti-PD-L1 | 1 | 0 | — | 1 |
| 250 µg rintatolimod + Anti-PD-L1 | 1 | 2 | 70% and 86% | 3 |

*Tumor assessments were performed per RECIST v1.1. criteria.

Example 5: Colorectal Cancer

Figure 7:
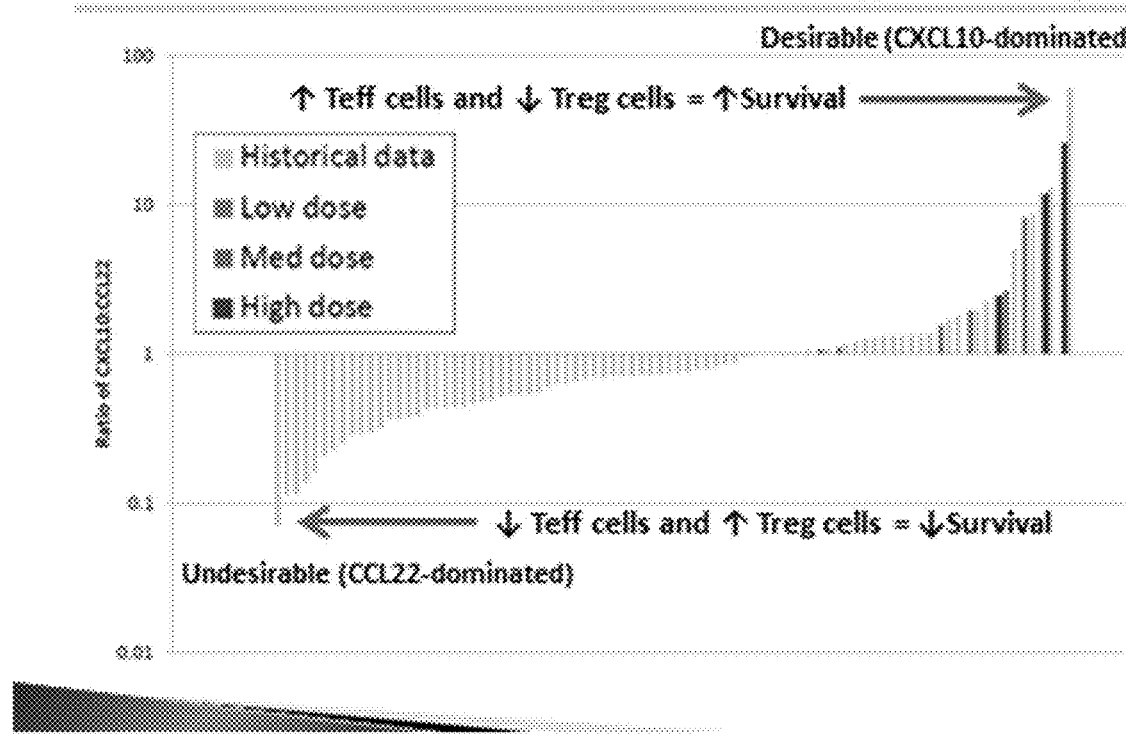
FIG. 7 depicts significantly improved ratio of CXCL10 ("good"):CCL22("bad") chemokines in tumor samples vs. historical data similarly collected (p=0.0015).
Figure 8:
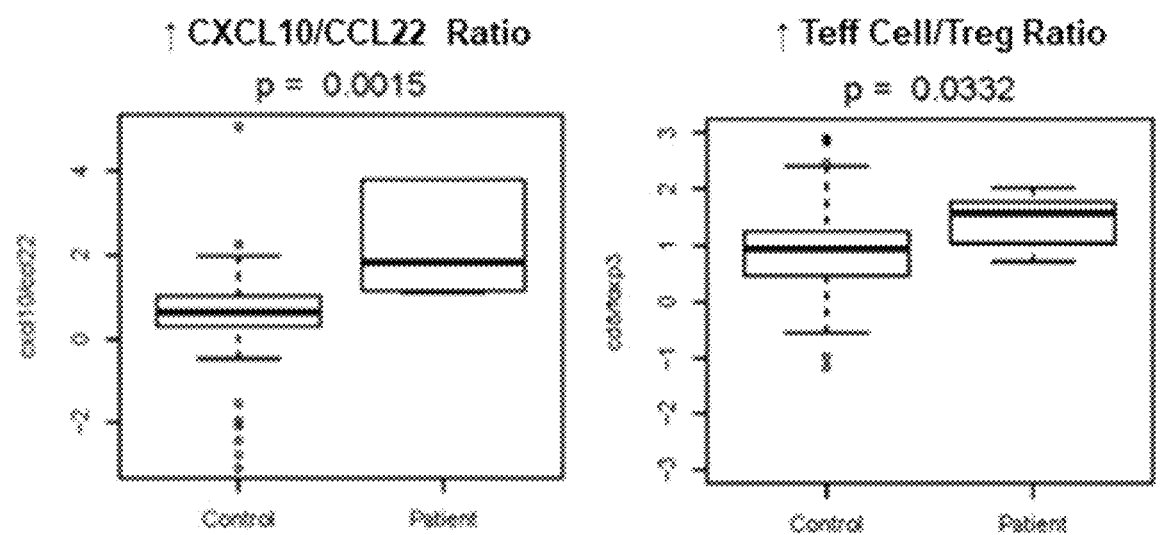
FIG. 8 depicts the ratios of chemokines and T cell markers in resected tumors following AMPLIGEN treatment (Phase I/II Patients vs. Historical Controls)

Similar to the pancreatic cancer success above, we also see positive results with colorectal cancer. As shown in Figures G and H, a Phase I/II colorectal carcinoma trial of AMPLIGEN plus rIFNa-2b and celecoxib produced an increased ratio of CXCL10 to CCL22 in the TME along with an increase in the ratio of Teff/Treg markers in 9 Patients with metastatic colorectal carcinoma compared to historical controls. See FIG. 7 depicts significantly improved ratio of CXCL10("good"):CCL22("bad") chemokines in tumor samples vs. historical data similarly collected (p=0.0015). See, also, FIG. 8 which depicts the ratios of chemokines and T cell markers in resected tumors following AMPLIGEN treatment (Phase I/II Patients vs. Historical Controls).

We therefore see that AMPLIGEN (rintatolimod) shows an ability to convert "cold" tumors into "hot" tumors which should be much more likely to respond to checkpoint blockage.

Figure 9:
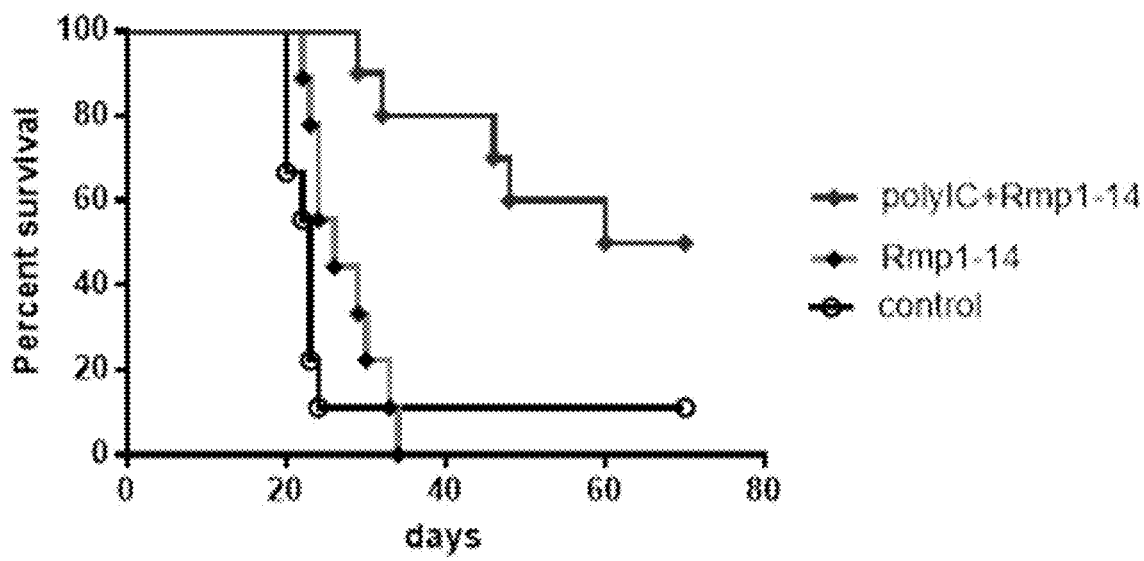
FIG. 9 depict a combination of AMPLIGENt plus anti-PD-1, increasing survival of greater than 250% compared to anti-PD-1 alone.

We also found that AMPLIGEN Plus Checkpoint Blockage Synergistically Increased Survival in c and Colorectal Carcinoma In a mouse model of colorectal carcinoma, the combination of AMPLIGEN plus anti-PD-1 showed a median survival increase of greater than 250% compared to anti-PD-1 alone. See, FIG. 9.

Example 6: Bladder Carcinoma

Similar to the pancreatic cancer success above, we also see positive results with bladder carcinoma.

AMPLIGEN significantly inhibited the growth of human bladder tumor xenografts in nude mice and appeared to work, at least in part, by an immune enhancing mechanism.

Example 7: Renal Carcinoma

Similar to the pancreatic cancer success above, we also see positive results with renal carcinomas (also referred to in this disclosure as renal cell cancer, renal cell carcinoma, kidney cancer).

Renal Cell Carcinoma

Antitumor activity of AMPLIGEN on human renal cell carcinoma xenografts in nude mice. Mismatched dsRNA caused statistically significant tumor growth inhibition (p<0.001) and survival (p<0.002) (Hubbell, 1990).

Figure 10:
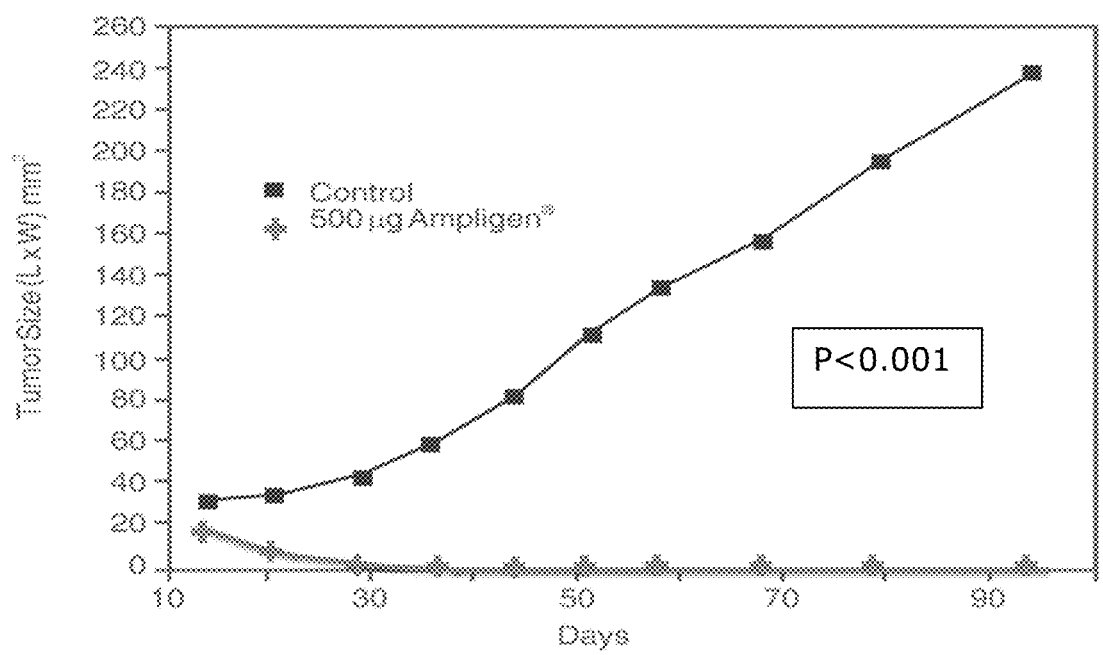
FIG. 10 depicts the growth inhibition of 786-0 xenografts.
Figure 11:
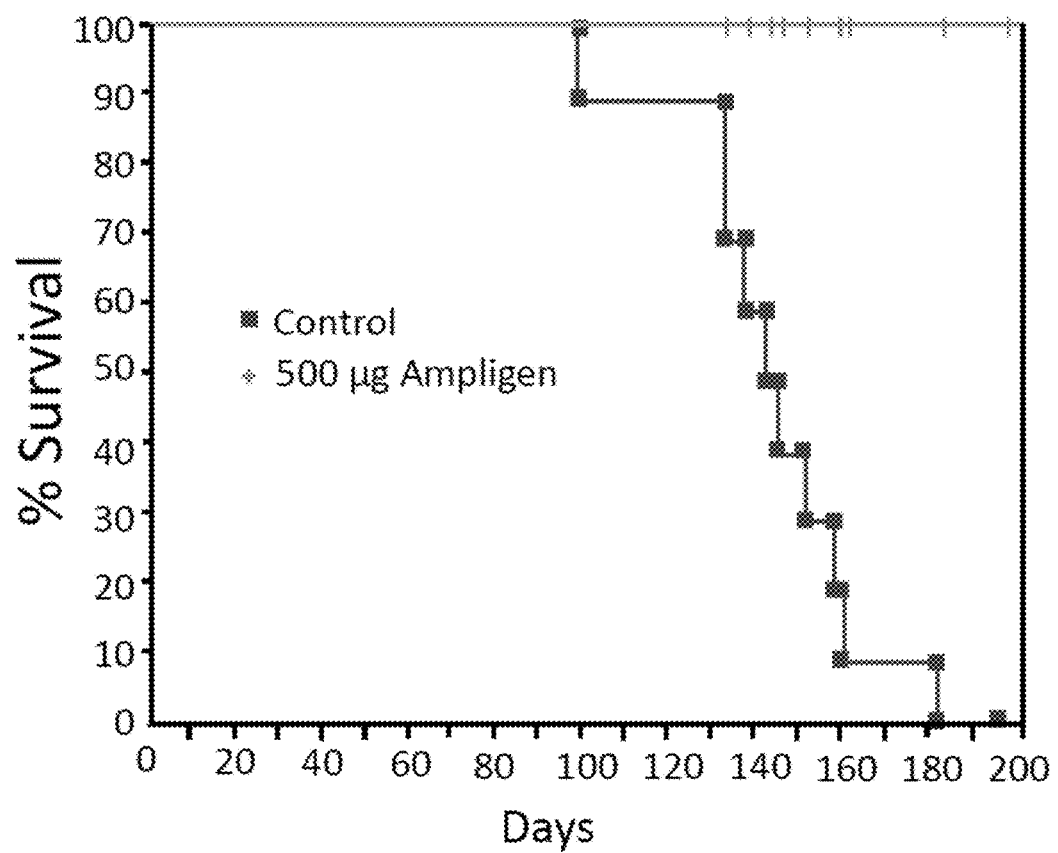
FIG. 11 depicts the survival of tumor-bearing nude mice 786-0 xenografts treated with AMPLIGEN.

FIGS. 10 and 11 illustrates results of rintatolimod (AMPLIGEN®) given as a monotherapy, where rintatolimod demonstrated an ability to increase anti-tumor immune mechanisms and survival. Results indicate that rintatolimod has direct anti-tumor effects and its augmentation of innate immune responses (NK cells) could have a key role in tumor regression. As shown in FIGS. 10 and 11, rintatolimod was effective at both inhibiting tumor growth (tumor regression was observed in each mouse) and increasing survival, where 90% of mice given rintatolimod were free of residual tumor while 100% of the control group had died.

Example 8: Combinatorial Immunotherapy of AMPLIGEN® (Rintatolimod) Poly I: Poly C12U and Blockade of Programmed Death-Ligand 1 Against Established Melanoma Tumors in a Mouse Model In this experimental sample, we were able to show that AMPLIGEN induced anti-tumor synergy when it is administered with checkpoint blockade. Specifically, we found that:

(1) AMPLIGEN was synergistic with anti-PD-L1, yielding an increased anti-tumor response in a B16 mouse melanoma model.

(2) The anti-tumor effect was significantly greater for the AMPLIGEN 250 µg+anti-PD-L1 cohort compared to anti-PD-L1 cohort alone (p=0.023).

(3) addition of AMPLIGEN to anti-PD-L1 increased the objective response rate of 300%, from 10% with anti-PD-L1 alone to 30% with the combination. The studies were conducted as follows:

AMPLIGEN and anti-PD-L1 antibodies were tested for anti-tumor activity against established subcutaneous B16 melanoma tumors in C57BL/6 mice. Briefly, mice (10 animals per group) were inoculated with 0.4×10E6 (i.e., 400,000) B16-F10 tumor cells in their shaved rear flanks. Seven days later, mice were randomized to six treatment groups as follows: (Group 1) No treatment (negative controls); (Group 2) AMPLIGEN alone 100 µg/dose 4λ; (Group 3) AMPLIGEN alone 250 µg/dose 4λ; (Group 4) Anti-PD-L1 mAb alone; (Group 5) AMPLIGEN 100 µg/dose 4× plus anti-PD-L1 mAb; (Group 6) AMPLIGEN 250 µg/dose 4× plus anti-PD-L1 mAb. mAb refers to monoclonal antibody.

AMPLIGEN was injected IV at 100 or 250 µg/dose 4 times, 5 days apart. Anti-PD-L1 mAb was administered IP on Days 1 and 3 after each AMPLIGEN dose at 200 µg/dose. Tumors were measured 3 times per week using calipers, measuring 2 opposing diameters. Mice exhibiting ulcerated tumors or tumors greater than 2 cm in diameter were euthanized starting on day 14. This confounded the analysis of tumor sizes after day 12. Results were presented as tumor sizes for individual mice throughout time of therapy up to Day 30.

The data shows that AMPLIGEN 250 µg+anti-pd-11 cohort had more than one significant tumor regression as seen in the chart below:

Only the AMPLIGEN 250 µg+anti-PD-L1 Cohort had More than One Significant Tumor Regression at Day 30*

| Group (n = 10) | Number of Complete Responses (CR) | Number of Partial Responses (PRs) | % Tumor Reduction in PRs | Total # Tumor Responses CR + PR |
|---|---|---|---|---|
| No Treatment Control | 0 | 0 | — | 0 |
| 100 µg AMPLIGEN | 0 | 0 | — | 0 |
| 250 µg AMPLIGEN | 0 | 0 | — | 0 |
| Anti-PD-L1 | 10% | 0 | — | 10% |
| 100 µg AMPLIGEN + Anti-PD-L1 | 10% | 0 | — | 10% |
| 250 µg AMPLIGEN + Anti-PD-L1 | 10% | 20% | 70% and 86% | 30% |

Tumor assessments were performed per RECIST v1.1 criteria

In addition, we observed synergistic effects by day 9 as follows:

Changes in Tumor Size at Day 9: Synergistic Effect of Combining AMPLIGEN+Anti-PD-L1 (p=0.023+).

Changes in Tumor Size from Day $0^\Delta$ to Day 9; Tumor Size Changes measured in $mm^2$

| Mouse # | Anti-PD-L1 Only | AMPLIGEN 250 µg + Anti PD-L1 |
|---|---|---|
| 1 | 1.10 (CR) | −15.66* |
| 2 | −12.19* | −2.27* (PR) |
| 3 | 61.99 | 22.88 |
| 4 | −3.48* | 25.35 |
| 5 | 78.44 | −11.28* (PR) |
| 6 | 55.94 | −13.51* (CR) |
| 7 | 4.65 | −18.33* |
| 8 | 23.15 | −10.48* |
| 9 | 49.56 | −14.20* |
| 10 | 0.09 | 9.77 |
| Totals | 259.3 | −27.7* |

*Negative values (i.e., tumors decreased in size)
+ ANOVA
$^\Delta$First tumor size measurement and first dose of AMPLIGEN occurred on Day 0

Synergism was also seen in a decrease in tumor size at follows:

A Significantly Greater Number of Tumors in the AMPLIGEN 250 µg + Anti-PD-L1 Cohort Decreased in Size
Comparison of the Number of Tumors Which Decreased in Size at Day 9 Compared to Day $0^\Delta$

| Mouse Cohort | Number of Tumors Increased in Size | Number of Tumors Decreased in Size | p-value |
|---|---|---|---|
| No Treatment Control (n = 10) | 10 | 0 | 0.0025* |
| Anti-PD-L1 Only (n = 10) | 8 | 2 | 0.0025* |
| 250 µg AMPLIGEN + Anti-PD-L1 (n = 10) | 3 | 7 | 0.0025* |

*Fisher's Exact Test (2-sided)
$^\Delta$First tumor size measurement and first dose of AMPLIGEN occurred on Day 0

Increase in Tumor Size at Day 12 was 5.2 Times Greater in the Anti-PD-L1 Cohort Compared to the AMPLIGEN 250 µg+Anti-PD-L1 Cohort (p=0.023±)

Changes in Tumor Size from Day 0° to Day 12

| Mouse # | Tumor Size Change ($mm^2$) Anti-PD-L1 Only | AMPLIGEN 250 µg + Anti PD-L1 |
|---|---|---|
| 1 | −5.16* (CR) | −7.45* |
| 2 | −10.13* | −8.33* (PR) |
| 3 | 153.54 | 46.78 |
| 4 | 14.85 | 48.65 |
| 5 | 167.07 | −11.00* (PR) |
| 6 | 153.78 | −13.74* (CR) |
| 7 | 31.06 | 7.28 |
| 8 | 33.35 | −0.98* |
| 9 | 79.55 | −5.34* |
| 10 | −1.78* | 62.81 |
| Mean Tumor Size | 61.6 | 11.9 |

*Negative values (i.e., tumors decreased in size)
+ ANOVA
$^\Delta$First tumor size measurement and the first dose of AMPLIGEN occurred on Day 0

In conclusion, AMPLIGEN was synergistic with anti-PD-L1 yielding an increased anti-tumor response in this melanoma model. At both Days 9 and 12 the anti-tumor effect was significantly greater for the AMPLIGEN 250 µg+anti-PD-L1 cohort compared to anti-PD-L1 cohort alone (p=0.023). Tumor reductions were seen at Days 9 and 12 in the AMPLIGEN 250 µg+anti-PD-L1 cohort translated into 1 CR and 2 PRs by Day 30. Thus, compared to the one CR seen in the anti-PD-L1 alone cohort, or a 10% overall response rate, the AMPLIGEN 250 µg+anti-PD-L1 cohort had a 30% overall response rate at Day 30.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

INCORPORATION BY REFERENCE

All publications, patent applications, and patents mentioned herein are hereby incorporated by reference in their entirety as if each individual publication or patent was specifically and individually indicated to be incorporated by reference. In case of conflict, the present application, including any definitions herein, will control.

We claim:

1. A method for treating a cancer selected from the group consisting of: pancreatic cancer; renal cell carcinoma; colorectal cancer and melanoma, in a subject in need thereof, the method comprising: administering to the subject at least a first compound and a second compound together or separately, wherein the first compound comprises an effective amount of an anti-PD-L1 antibody optionally with at least one pharmaceutically-acceptable carrier, and wherein the second compound is an effective amount of rintatolimod optionally with at least one pharmaceutically-acceptable carrier.

2. The method of claim 1 wherein treating a cancer comprises at least one selected from the group consisting of inhibiting a proliferation of a tumor in a subject; initiating, enhancing or prolonging the effects of a checkpoint inhibitor in a subject; and activating a response to a checkpoint inhibitor in the subject, wherein the tumor is a tumor from a cancer selected from the group consisting of: pancreatic cancer; renal cell carcinoma; colorectal cancer and melanoma.

3. The method of claim 1 wherein the cancer is malignant, non-malignant, metastatic, or non-metastatic.

4. The method of claim 1 wherein the effective amount of rintatolimod is a synergistic, therapeutically effective amount.

5. The method of claim 1 wherein the combination of rintatolimod and the anti-PD-L1 antibody provides a synergistic effect in the treatment of the cancer or in the inhibition of the proliferation of tumor cells, wherein the tumor cells are from a cancer selected from the group consisting of: pancreatic cancer; renal cell carcinoma; colorectal cancer and melanoma.

6. The method of claim 1 wherein the synergistic effect is selected from the group consisting of: inhibiting tumor growth; inducing tumor cell death; increasing tumor regression; preventing tumor recurrence; preventing tumor growth; preventing tumor spread; delaying tumor recurrence; delaying tumor growth; delaying tumor spread; and promoting tumor elimination, wherein the tumor is a tumor from a cancer selected from the group consisting of: pancreatic cancer; renal cell carcinoma; colorectal cancer and melanoma.

7. The method of claim 1 wherein the effective amount of anti-PD-L1 antibody is a synergistic, therapeutically effective amount.

8. The method of claim 1 wherein the anti-PD-L1 antibody administered provides an additive or synergistic effect in the treatment of a cancer or an inhibition of a proliferation of a tumor, wherein the tumor is a tumor from a cancer selected from the group consisting of: pancreatic cancer; renal cell carcinoma; colorectal cancer and melanoma.

9. The method of claim 1 wherein the rintatolimod and the anti-PD-L1 antibody are administered together or separately within two hours.

10. The method of claim 1 further comprising administering to the subject a third compound wherein the third compound is one or more selected from the group consisting of: a chemotherapeutic drug, a targeted drug anti-cancer drug, and a targeted anti-cancer drug comprising an antibody.

11. The method of claim 10 wherein the effective amount of third compound is a synergistic, therapeutically effective amount.

12. The method of claim 10 wherein the third compound acts synergistically with the rintatolimod and the anti-PD-L1 antibody.

13. The method of claim 1 further comprising administering to the subject one or more selected from the group consisting of: an interferon, interferon mixture, and alpha-interferon species.

14. The method of claim 13 wherein the alpha-interferon species were purified as a mixture of at least seven species of a-interferon produced by human white blood cells.

15. The method of claim 13 wherein said alpha-interferon species comprises alpha interferon species alpha 2, alpha 4, alpha 7, alpha 8, alpha 10, alpha 16 and alpha 17.

16. The method of claim 1 wherein at least one of the compounds is administered intravenously.

17. The method of claim 1 wherein the rintatolimod and the anti-PD-L1 antibody are administer separately but within a time period selected from the group consisting of: 1 month, 1 week, 3 days, 1 day, 12 hours, 6 hours, 3 hours, 2 hours, 1 hour, and 30 minutes.

18. The method of claim 1 wherein the at least two of the compounds are in a single composition.

19. The method of claim 1 wherein the rintatolimod and the anti-PD-L1 antibody together provides a synergistic effect in the treatment of cancer or in an inhibition of a proliferation of tumor cells over the administration of rintatolimod alone, anti-PD-L1 antibody alone, or sum of rintatolimod alone and anti-PD-L1 antibody alone, wherein the tumor cells are from a cancer selected from the group consisting of: pancreatic cancer; renal cell carcinoma; colorectal cancer and melanoma.

20. The method of claim 1 wherein the anti-PD-L1 antibody has at least one characteristic selected from the group consisting of: an antibody; a monoclonal antibody; a humanized antibody; a fully human antibody; a fusion protein; a PEGylated antibody; a multimeric antibody; an antibody fragment comprising an epitope binding region; and a combination thereof.

21. The method of claim 1 wherein the anti-PD-L1 antibody is selected from the group consisting of: atezolizumab; avelumab; BMS-936559 (MDX-1105); durvalumab (MEDI-4736); and a combination thereof.

22. The method of claim 1 wherein the first compound or the second compound is a solid or a liquid formulation.

23. The method of claim 1 wherein the subject is a mammal.

24. The method of claim 23 wherein the mammal is a human.

25. The method of claim 1 wherein the subject has a cancer that is ineffective to treatment by anti-PD-L1 antibody alone and/or that is ineffective to a chemotherapeutic drug alone.

26. A method for treating a cancer selected from the group consisting of: pancreatic cancer; renal cell carcinoma; colorectal cancer and melanoma in a subject in need thereof, the method comprising: contacting the cancer to a first compound and a second compound together or separately, wherein the first compound comprises an effective amount of an anti-PD-L1 antibody optionally with at least one pharmaceutically-acceptable carrier, and wherein the second compound is an effective amount of rintatolimod optionally with at least one pharmaceutically-acceptable carrier.

27. The method of claim 10 wherein the chemotherapeutic drug is at least one selected from the group consisting of: fluorouracil, epirubicin, and cyclophosphamide (FEC); fluorouracil, epirubicin, cyclophosphamide and docetaxel (FEC-T); abiraterone acetate; abiraterone; actinomycin D; doxorubicin, cyclophosphamide and etoposide (ACE); afatinib; aflibercept; aldesleukin; alemtuzumab; amsacrine; anastrozole; arsenic trioxide; asparaginase; axitinib; azacitidine; bendamustine; bevacizumab; bexarotene; bicalutamide; bleomycin, etoposide, doxorubicin, cyclophosphamide, vincristine, procarbazine, and prednisone (BEACOPP); bleomycin, etoposide and platinum (BEP); bleomycin; bortezomib, doxorubicin and dexamethasone (PAD); bortezomib; bosutinib; brentuximab; buserelin; busulfan; cabazitaxel; cabozantinib; capecitabine and oxaliplatin (CAPDX or XELOX); capecitabine; carboplatin and etoposide; carboplatin and paclitaxel; carboplatin; carmustine, etoposide, cytarabine and melphalan (BEAM); carmustine; ceritinib; cetuximab; chlorambucil, vinblastine, procarbazine and prednisolone (CHLVPP); chlorambucil; cisplatin and capecitabine (CX); cisplatin tegafur, gimeracil and oteracil; cisplatin, etoposide and ifosfamide (IPE or PEI); cisplatin, fluorouracil and trastuzumab; cisplatin, methotrexate and vinblastine (CMV); cisplatin, vincristine, methotrexate, bleomycin, actinomycin D, cyclophosphamide and etoposide (POMB/ACE); cisplatin; cladribine; clodronic acid; clofarabine; codeine and paracetamol; crizotinib; cyclophosphamide and rituximab (FCR); cyclophosphamide, doxorubicin and vincristine (CAV); cyclophosphamide, doxorubicin, vincristine and etoposide (CAVE); cyclophosphamide, doxorubicin, vincristine and prednisolone (CHOP); cyclophosphamide, methotrexate and fluorouracil (CMF); cyclophosphamide, thalidomide and dexamethasone (CTD); cyclophosphamide, vincristine, and prednisone (CVP); cyclophosphamide; cyproterone acetate; cytarabine; cytosine arabinoside; dabrafenib; dacarbazine; dactinomycin; dasatinib; daunorubicin; decitabine; degarelix; denosumab; dexamethasone; diamorphine; dihydroxyacetone phosphate; disodium pamidronate; docetaxel, cisplatin and fluorouracil (TPF); docetaxel, doxorubicin and cyclophosphamide (TAC); docetaxel; doxorubicin and cyclophosphamide (AC); doxorubicin and ifosfamide (DOXIFOS); doxorubicin in liposome-encapsulated forms; doxorubicin, bleomycin, vinblastine and dacarbazine (ABVD); doxorubicin; eldisine; enzalutamide; epirubicin and cyclophosphamide (EC); epirubicin, cisplatin and capecitabine (ECX); epirubicin, carboplatin and capecitabine (ECARBOX); epirubicin, cisplatin and fluorouracil (ECF); epirubicin, oxaliplatin and capecitabine (EOX); epirubicin, oxaliplatin and fluorouracil (EOF); epirubicin; eribulin; erlotinib; estramustine phosphate; etoposide and cisplatin (EP); etoposide, methylprednisolone succinate, high dose cytarabine and cisplatin (ES-HAP); etoposide; everolimus; exemestane; fentanyl; flavin adenine dinucleotide (FAD); fludarabine; fludarabine, mitoxantrone and dexamethasone (FMD); fludarabine; fluorouracil; fluorouracil and leucovorin calcium; flutamide; folinic acid, fluorouracil, irinotecan, and oxaliplatin (FOLFIRINOX); leucovorin, fluorouracil, and oxaliplatin (FOLFOX); folinic acid, fluorouracil and irinotecan (FOLFIRI); fulvestrant; gefitinib gemcitabine and carboplatin (GEMCARBO); gemcitabine and capecitabine; gemcitabine and cisplatin (GC); gemcitabine and paclitaxel; gemcitabine; goserelin; granulocyte colony stimulating factor (G-CSF); hydroxyurea; ibandronic acid; ibritumomab tiuxetan; ibritumomab; ibrutinib; ibuprofen; idarubicin and dexamethasone (Z-DEX); idarubicin; idelalisib; ifosfamide, carboplatin and etoposide (ICE); ifosfamide; imatinib; imiquimod; interferon; interleukin; interleukin-2; interferon alfa; ipilimumab; irinotecan and capecitabine; irinotecan; lanreotide; lapatinib; lenalidomide; letrozole; leuprorelin acetate; leuprorelin; liposomal cytarabine; liposomal doxorubicin; lomustine; medroxyprogesterone acetate; megestrol acetate; melphalan, prednisolone and thalidomide (MPT); melphalan; mercaptopurine; methotrexate, vinblastine sulfate, doxorubicin hydrochloride and cisplatin (MVAC); methotrexate; methyl-prednisolone; mifamurtide; mitomycin C, ifosfamide and cisplatin (MIC); mitomycin C; mitomycin C, vinblastine and cisplatin (MVP); mitotane; mitoxantrone; mitoxantrone, mitomycin c and methotrexate (MMM); morphine sulfate; morphine; nab-paclitaxel; nelarabine; nilotinib; nintedanib; nivolumab; obinutuzumab; octreotide; ofatumumab; olaparib; oxaliplatin and capecitabine; oxaliplatin; paclitaxel and carboplatin (PC); paclitaxel and carboplatin; paclitaxel and epirubicin (PE); paclitaxel, ifosfamide and cisplatin (TIP); pamidronate disodium; panitumumab; paracetamol; pazopanib; pembrolizumab; pemetrexed and carboplatin; pemetrexed and cisplatin; pemetrexed; pentostatin; pertuzumab; pixantrone; pomalidomide; ponatinib; prednisolone, mitoxantrone, cyclophosphamide, etoposide, bleomycin and vincristine (PMITCEBO); prednisolone; procarbazine, lomustine and vincristine (PCV); protein-bound paclitaxel; raloxifene; raltitrexed; regorafenib; rituximab, cyclophosphamide, doxorubicin hydrochloride, vincristine and prednisolone (R-CHOP); rituximab, cyclophosphamide, vincristine and prednisolone (R-CVP); rituximab, dexamethasone, cytarabine and cisplatin (R-DHAP); rituximab, etoposide, methylprednisolone succinate, high dose cytarabine and cisplatin (R-ESHAP); rituximab, gemcitabine, cyclophosphamide, vincristine and prednisolone (R-GCVP); rituximab, ifosfamide, carboplatin and etoposide (RICE); rituximab; sorafenib; steroid; streptozocin; sunitinib; tamoxifen; docetaxel and cyclophosphamide (TC); tegafur, gimeracil and oteracil; temozolomide; temsirolimus; thalidomide; thiotepa; tioguanine; tomudex; topotecan; trabectedin; trastuzumab emtansine; trastuzumab; treosulfan; tretinoin; triptorelin; vandetanib; vemurafenib; vinblastine, ifosfamide and cisplatin (VEIP); vinblastine; vincristine, actinomycin D and ifosfamide (VAI); vincristine, actinomycin D and cyclophosphamide (VAC); vincristine, doxorubicin and dexamethasone (VAD); vincristine, ifosfamide, doxorubicin and etoposide (VIDE); vincristine; vindesine; vinflunine; vinorelbine; vismodegib; and zoledronic acid.

28. The method of claim 1, wherein the rintatolimod is a stabilized polymer.

29. The method of claim 28, wherein the rintatolimod is stabilized with lysine cellulose.

* * * * *